US009619727B2

(12) United States Patent
Nagatomo et al.

(10) Patent No.: US 9,619,727 B2
(45) Date of Patent: Apr. 11, 2017

(54) MATCHING PROCESS DEVICE, MATCHING PROCESS METHOD, AND INSPECTION DEVICE EMPLOYING SAME

(71) Applicant: Hitachi High-Technologies Corporation, Minato-ku, Tokyo (JP)

(72) Inventors: Wataru Nagatomo, Tokyo (JP); Yuichi Abe, Tokyo (JP); Hiroyuki Ushiba, Tokyo (JP)

(73) Assignee: Hitachi High-Technologies Corporation, Minato-ku, Tokyo (JP)

( * ) Notice: Subject to any disclaimer, the term of this patent is extended or adjusted under 35 U.S.C. 154(b) by 95 days.

(21) Appl. No.: 14/417,425

(22) PCT Filed: Jul. 16, 2013

(86) PCT No.: PCT/JP2013/069296
§ 371 (c)(1),
(2) Date: Jan. 26, 2015

(87) PCT Pub. No.: WO2014/017337
PCT Pub. Date: Jan. 30, 2014

(65) Prior Publication Data
US 2015/0199583 A1    Jul. 16, 2015

(30) Foreign Application Priority Data

Jul. 27, 2012  (JP) .................. 2012-167363

(51) Int. Cl.
*G06K 9/32* (2006.01)
*G06T 7/00* (2017.01)
(Continued)

(52) U.S. Cl.
CPC ..... *G06K 9/3216* (2013.01); *G01N 21/95607* (2013.01); *G06K 9/623* (2013.01);
(Continued)

(58) Field of Classification Search
None
See application file for complete search history.

(56) References Cited

U.S. PATENT DOCUMENTS

| 6,627,888 | B2 | 9/2003 | Yamaguchi et al. |
| 6,647,139 | B1 | 11/2003 | Kunii et al. |

(Continued)

FOREIGN PATENT DOCUMENTS

| JP | 5-101186 A | 4/1993 |
| JP | 9-138785 A | 5/1997 |

(Continued)

OTHER PUBLICATIONS

International Search Report (PCT/ISA/210) dated Oct. 8, 2013 with English translation (five pages).

(Continued)

*Primary Examiner* — Sumati Lefkowitz
*Assistant Examiner* — David Perlman
(74) *Attorney, Agent, or Firm* — Crowell & Moring LLP

(57) ABSTRACT

An inspection device that performs pattern matching on a searched image performs matching between a template image of an inspection object and the searched image by using: a feature region extraction process unit that extracts a feature quantity from the template image acquired for learning; a feature quantity extraction process unit that extracts a feature quantity from the searched image acquired for learning; a mutual feature quantity calculation process unit that calculates a mutual feature quantity of the template image and the searched image from the feature quantity extracted from the template image and the feature quantity extracted from the searched image; a learning process unit that calculates, using a plurality of the mutual feature quantities, a discrimination boundary surface that determines matching success or failure; a process unit that (Continued)

calculates a plurality of the mutual feature quantities from an image acquired from the inspection object; and the plurality of mutual feature quantities and the discrimination boundary surface. Thus, an inspection device can be provided that outputs an accurate matching position in template matching even when there is a large apparent image discrepancy between the template and the searched image.

8 Claims, 19 Drawing Sheets

(51) Int. Cl.
  *G01N 21/956* (2006.01)
  *G06K 9/62* (2006.01)
  *G06K 9/00* (2006.01)

(52) U.S. Cl.
  CPC ............ *G06K 9/6215* (2013.01); *G06T 7/001* (2013.01); *G06T 7/0044* (2013.01); *G06K 9/0014* (2013.01); *G06T 2207/10004* (2013.01); *G06T 2207/10061* (2013.01); *G06T 2207/20081* (2013.01); *G06T 2207/30148* (2013.01)

(56) References Cited

U.S. PATENT DOCUMENTS

| | | | |
|---|---|---|---|
| 2006/0212413 A1* | 9/2006 | Rujan | ................. G06F 17/3071 706/20 |
| 2011/0135166 A1* | 6/2011 | Wechsler | ........... G06K 9/00288 382/118 |
| 2012/0087574 A1* | 4/2012 | Yokono | ................ G06K 9/6257 382/159 |

FOREIGN PATENT DOCUMENTS

| | | |
|---|---|---|
| JP | 2001-14465 A | 1/2001 |
| JP | 2001-243906 A | 9/2001 |
| JP | 2003-76976 A | 3/2003 |
| JP | 2006-292615 A | 10/2006 |
| JP | 2006-293528 A | 10/2006 |

OTHER PUBLICATIONS

Japanese-language Written Opinion (PCT/ISA/237) dated Oct. 8, 2013 (three pages).

"Digital Image Processing" (CG-ART Society) 2009, pp. 201-205, including partial English translation (five (5) pages).

Takagi et al., "Road Sign Recognition Using SIFT Feature" SII07, LD2-06, Jun. 2007, Yokohama, pp. 1-8, including partial English translation (11 pages).

Kondo et al., "Development of an Automated Patient-recognition Method for Digital Chest Radiographs Using Edge-enhanced Images" Japanese Journal of Radiological Technology, NII-Electronic Library Service, Oct. 2003, vol. 59, No. 10, pp. 1277-1284, including partial English translation (11 pages).

\* cited by examiner

FIG. 6
Matching score calculation
(a)
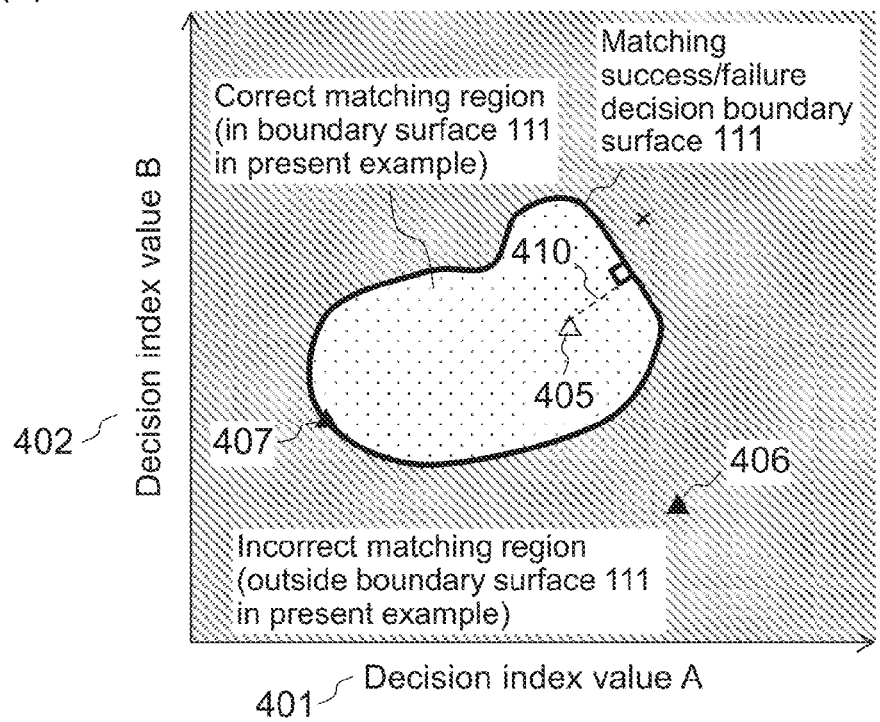
(b)
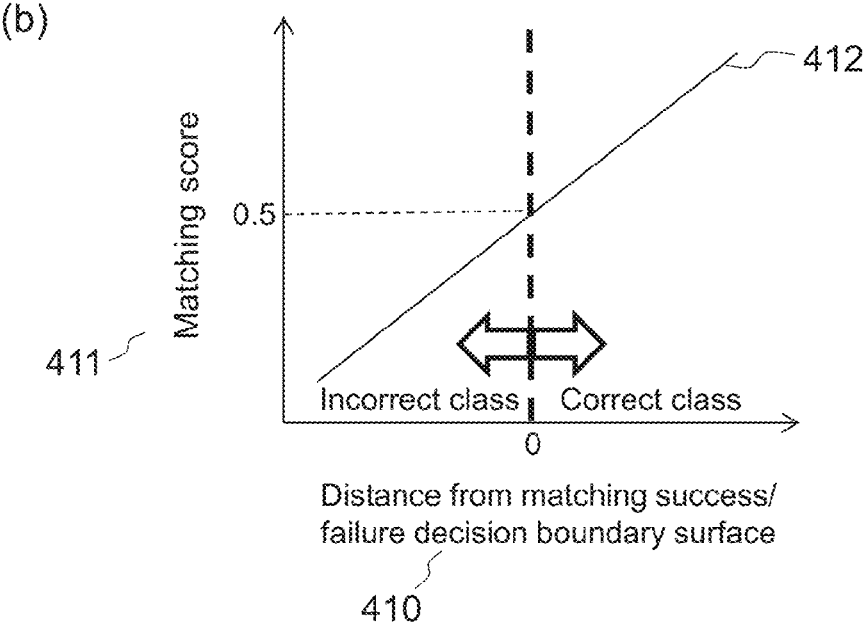

FIG. 7
Example of matching success/failure decision boundary surface designation (SVM)
(a)
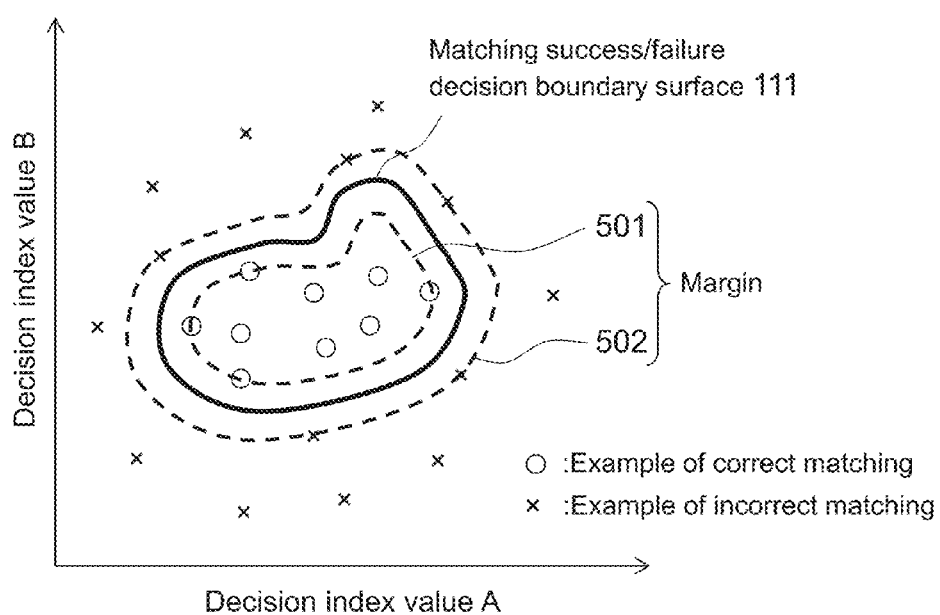
(b)
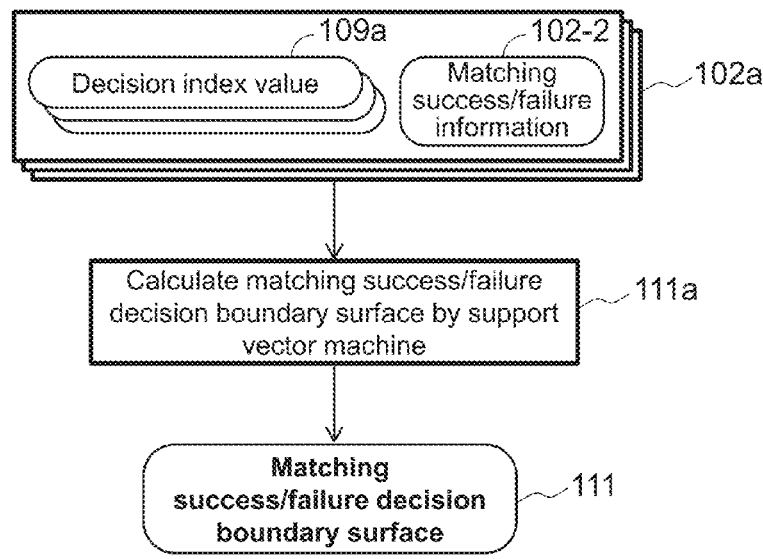

FIG. 9
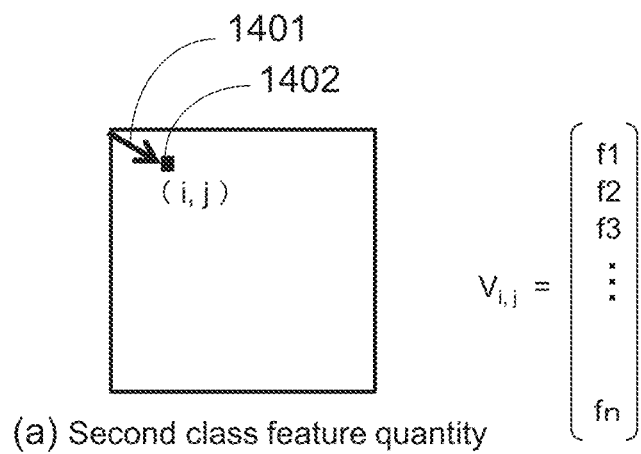
(a) Second class feature quantity
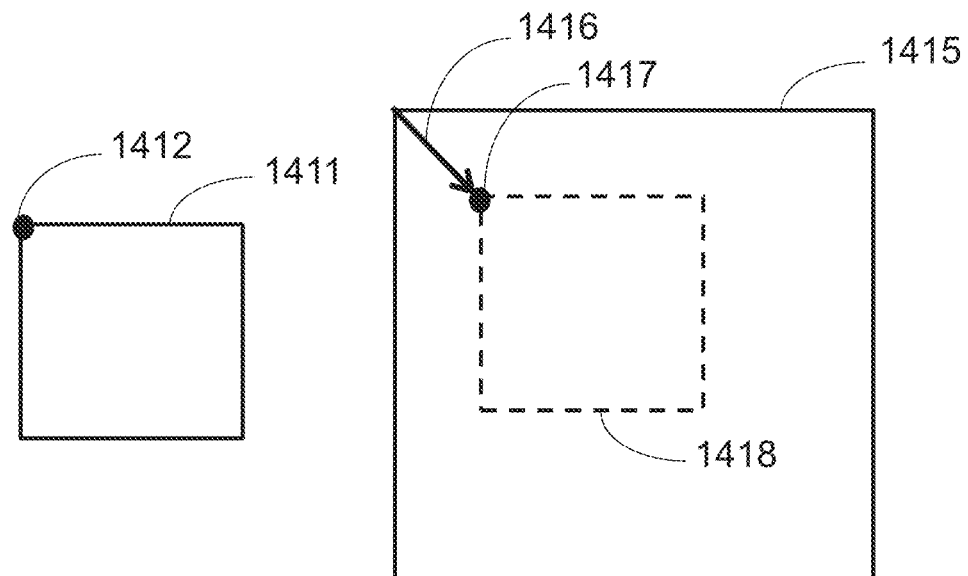
(b) Third class feature quantity Examples of second class feature quantity calculation region FIG. 11
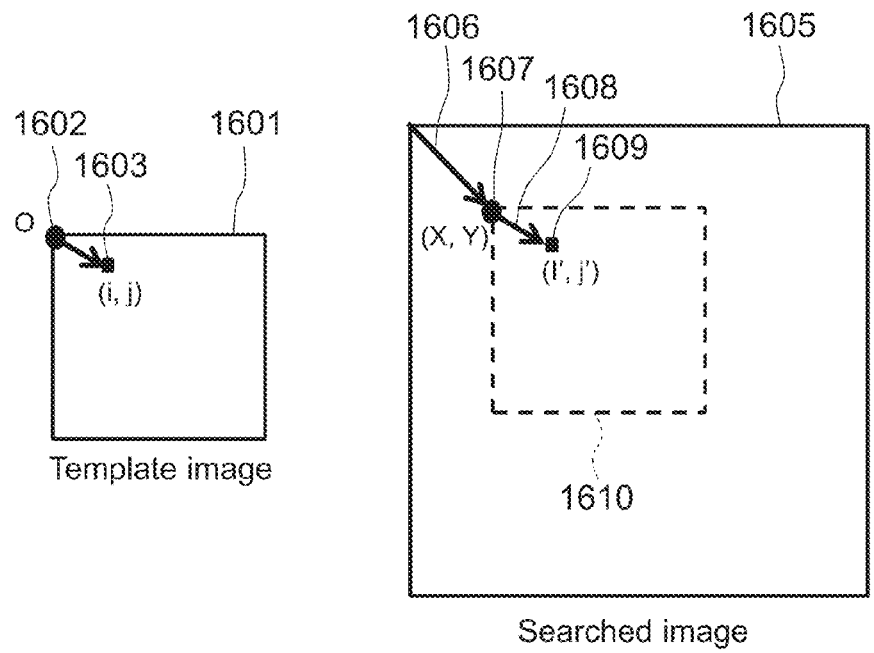
(a)
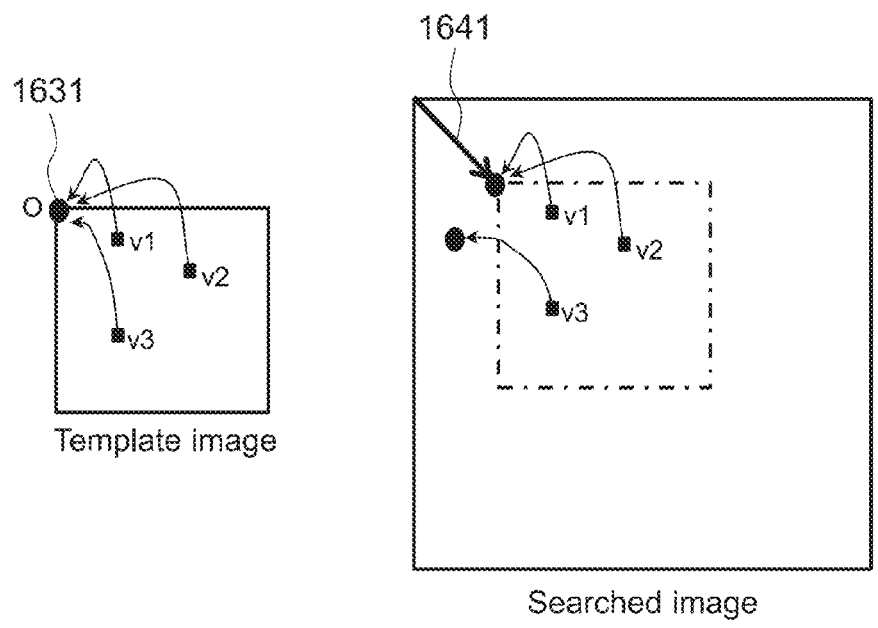
(b)

Histogram feature

Contrast feature

Contrast feature (contrast in image)

Line profile

Normalized correlation

SIFT

Corner

FIG. 14
Method of learning data feeding
(a) Template is common
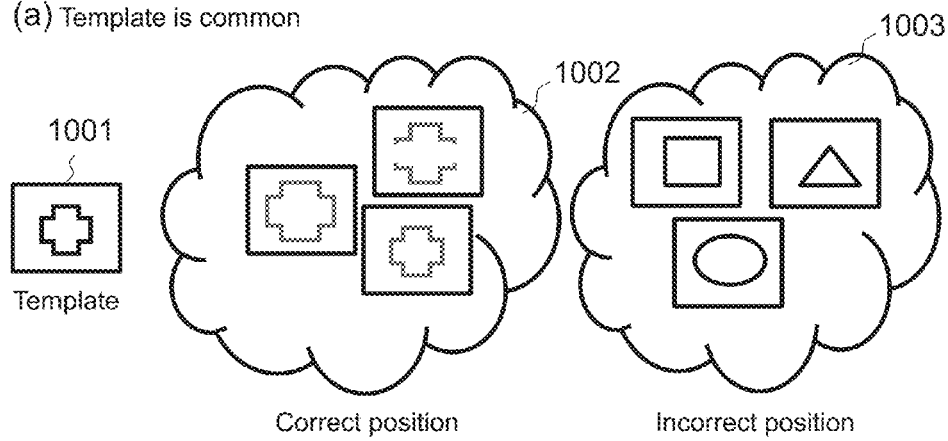
(b) Template variations
(purpose: to make sample distribution in index value space more versatile)
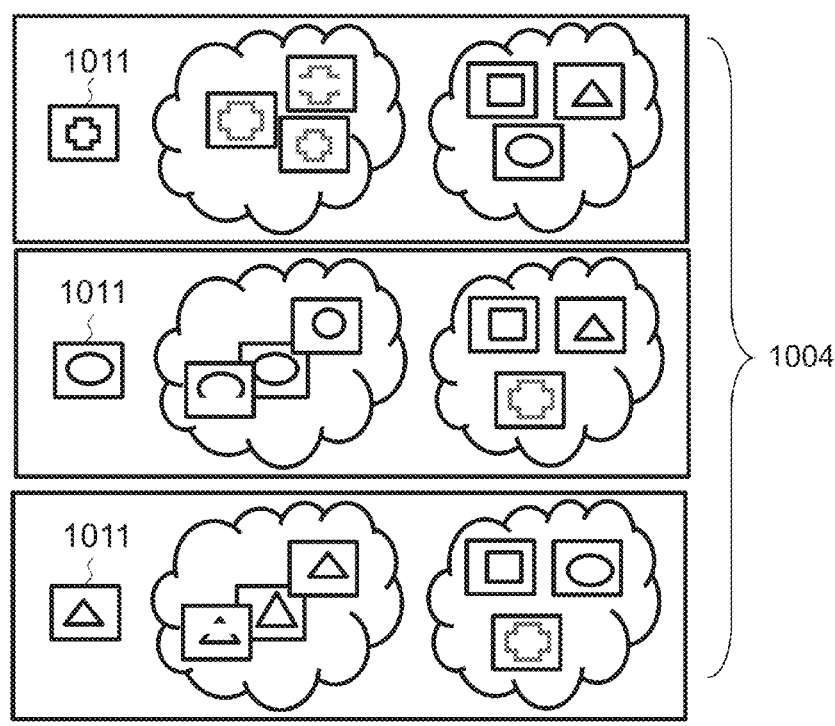

FIG. 16
Manual designation of matching success/failure decision boundary surface (score center value)
(a)
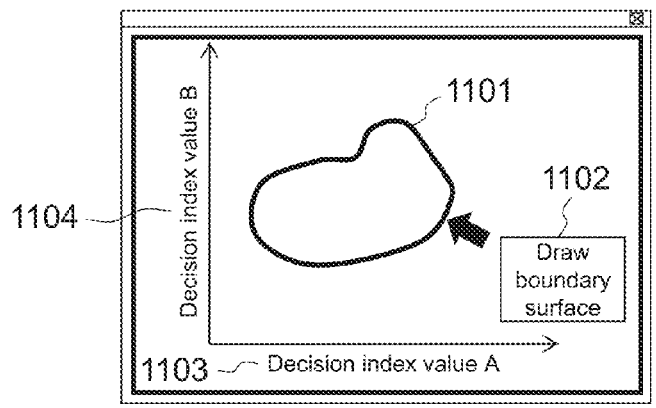
(b)　　　　　　　　　(c)
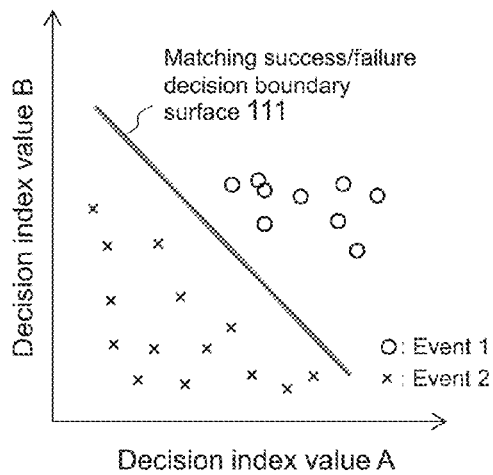 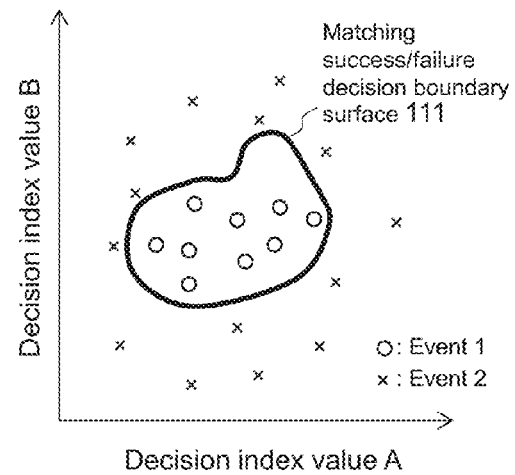

FIG. 17
Matching result stability confirmation process
(a)
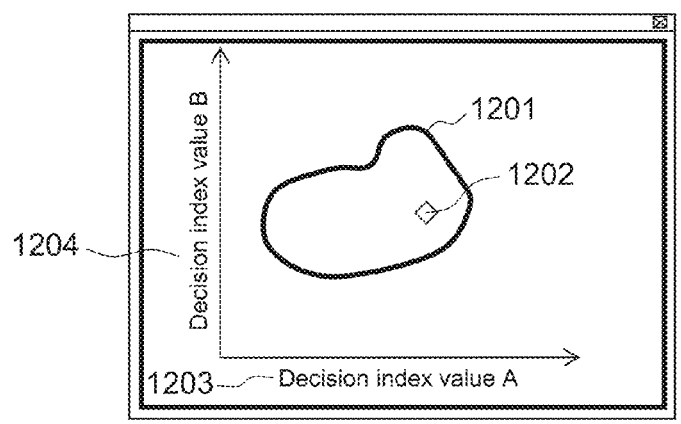
(b)
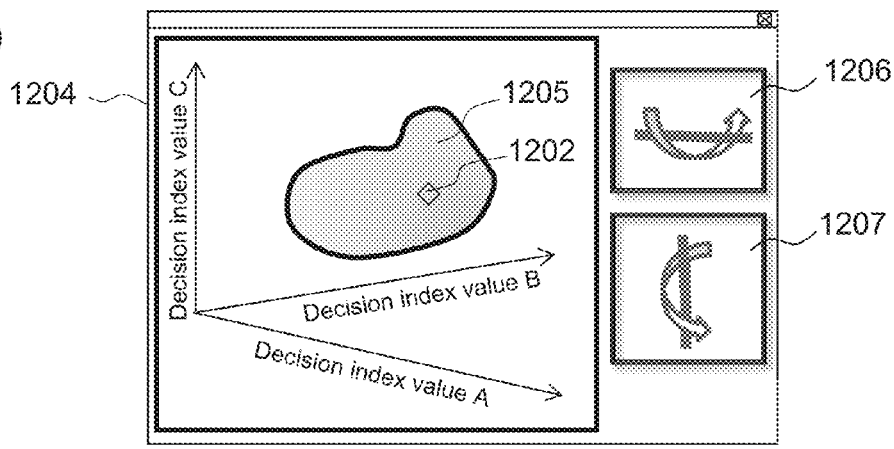
(c)
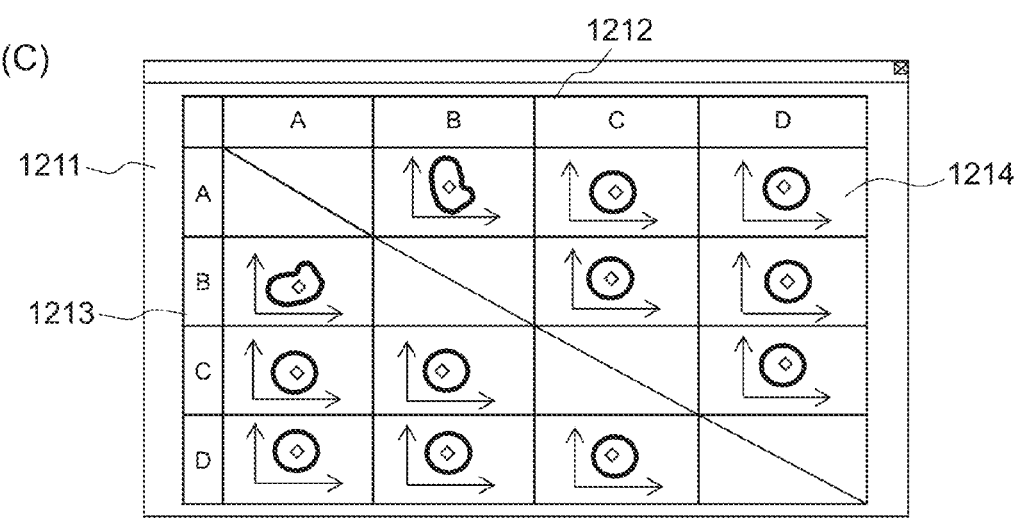

MATCHING PROCESS DEVICE, MATCHING PROCESS METHOD, AND INSPECTION DEVICE EMPLOYING SAME

TECHNICAL FIELD

The present invention relates to a matching process technology and more particularly to a pattern matching technology, particularly to a template matching technology in inspection technology for inspection or measurement of a pattern formed on a semiconductor wafer.

BACKGROUND ART

In a device for measuring and inspecting a pattern formed on a semiconductor wafer, a process is performed in which the field of view of the inspection device is aligned with a desired measuring position using template matching technology (see Non Patent Literature 1 indicated below) for matching using a template. In Patent Literature 1 indicated below, an example of such template matching method is described. The template matching process refers to a process of finding a region that most closely matches a pre-registered template image from an image as a search object.

In a specific example of the inspection device using template matching, a scanning electron microscope is used to measure the pattern on the semiconductor wafer. In the inspection device, while the field of view of the device is moved to a rough position for measuring, a large error is often caused on an image taken at a high magnification ratio by the electron microscope with only the stage positioning accuracy. Further, the wafer may not be placed on the stage in the same direction every time, and the coordinate system (such as the direction in which wafer chips and the like are arranged) of the wafer placed on the stage may not be completely aligned with the direction in which the stage is driven, creating causes for the error on the image taken at high magnification ratio by the electron microscope.

In order to obtain an electron microscope image of high magnification ratio at a desired observation position, the electron beam may be deflected by a fine amount (such as on the order of not more than several tens of µm) so as to irradiate a target position on the observed sample (which may be referred to as "beam shift"). However, even when the beam shift is performed, an error from the desired observation position may be caused with regard to the irradiation position with only the accuracy of beam deflection control. In order to perform measurement and inspection at an accurate position while correcting for such various errors, template matching is performed.

Specifically, alignment is performed in multiple stages including alignment using an optical camera having a lower magnification ratio than an electron microscope image, and alignment in an electron microscope image. For example, when the coordinate system of a wafer placed on the stage is aligned using the optical camera, images of a plurality of chips at positions spaced apart from each other on the wafer (such as chips at the left and right ends of the wafer) are used for alignment. First, a unique identical pattern in each chip or nearby (a pattern at the relatively same position in the respective chips) is registered as a template (the pattern used for the registration is often the one created as an optical alignment pattern on the wafer).

Then, the stage is moved so as to image the pattern for which template registration has been performed in each chip, and an image is acquired from each chip. The acquired images are subjected to template matching. Based on the respective matching positions obtained as a result of the matching, a stage movement error amount is calculated, and the coordinate system for stage movement and the wafer coordinate system are aligned using the error amount as a stage movement correction value. In the electron microscope alignment performed next, a unique pattern that is the closest to the measuring position is registered in advance as a template, and the relative coordinates of the measuring position as viewed from the template are stored. When the measuring position is determined from the image taken by the electron microscope, template matching is performed in the taken image to determine a matching position, and the measuring position is determined by moving from the matching position by the relative coordinates that have been stored. By utilizing such template matching, the field of view of the device is moved to the desired measuring position.

When the above-described stage movement error or the beam shift error is large, the alignment pattern may not be included within the image taken by the electron microscope. In this case, a process (measurement interruption) may be performed to again search for the alignment pattern around the imaged position (peripheral search) or to interrupt the measurement and inform the user via an alarm about the alignment failure, for example. In order to perform the process, it is necessary to determine whether the alignment pattern is present in the image. For the determination, a matching score in template matching (such as a correlation value in normalized correlation computation) is used, for example. If the matching score is greater than a pre-set reference value (which may be hereafter referred to as "score acceptance"), it is determined that the pattern is present in the field of view; if the matching score is lower than the score acceptance, it is determined that the pattern is absent.

The template matching method can be categorized into an image-based method by normalized correlation and the like, and a feature point-based technique comparing feature points extracted from images. In the former, image-based technique, an image of the same size as the template is cut out from a searched image, for example, and a correlation value between the cut-out image and the template is calculated. The correlation value is calculated for each image position cut out from the searched image (the position may be the entire searched image), and the position with a large correlation value is determined as a matching position (Non Patent Literature 1). On the other hand, in the latter, feature point-based technique, a plurality of feature points is extracted from each of the template and the searched image, and similar feature points are found out from the both images (corresponding point matching), for example. And the matching position is determined at a position at which the number of overlaps in projected regions is increased when the template is projected such that the feature points are overlapped (taking into consideration rotation and different scales and the like between the images) (Non Patent Literature 2).

CITATION LIST

Patent Literature

Patent Literature 1: Patent Literature 2001-243906 (corresponding to U.S. Pat. No. 6,627,888)

Non Patent Literature

Non Patent Literature 1: Digital Image Processing (CG-ART Society) p. 203-204 (2009)

Non Patent Literature 2: Takagi, Fujiyoshi, "Road Sign Recognition Using SIFT Feature", SII07, LD2-06 (2007)

Non Patent Literature 3: Kondo, Morishita, Katsuragawa, Doi, "Development of an Automated Patient-recognition Method for Digital Chest Radiographs Using Edge-enhanced Images", Japanese Journal of Radiological Technology, Vol. 59, No. 10, pp. 1277-1284 (2003)

SUMMARY OF INVENTION

Technical Problem

In the above-described template matching, matching may not be successful when there is a large apparent discrepancy between the template and the searched image. The apparent image discrepancy between the template and the searched image may be increased when, for example, there is a large difference between the imaging condition of the inspection device at the time of template registration and the photography condition of the inspection device when the searched image is taken; when there is a large difference in the quality of the semiconductor pattern when photographed at the time of template registration and the quality of the semiconductor pattern when the searched image was taken; or when the semiconductor pattern manufacturing step at the time of template registration is different from the semiconductor pattern manufacturing step at the time of photographing the searched image. These examples are not exhaustive, and the apparent image discrepancy between the template and the searched image may be increased by various factors.

In the case of the image-based template matching, if there is an apparent discrepancy between the template and the searched image, the correlation value at the correct matching position may be decreased, resulting in a matching failure. In order to decrease the apparent difference between the template and the searched image, preprocessing methods, such as smoothing process or edge enhancing, have been proposed (Non Patent Literature 3).

However, it is difficult to determine the correct matching position with respect to images with various appearances. For every different appearance of an image, the user needs to modify the score acceptance, decreasing the operation rate of the device. Ideally, the score acceptance has a unified value (fixed value); however, this is difficult with the current techniques. FIG. 4 shows an example of the correlation value (matching score) at a correct matching position and a incorrect matching position with respect to a plurality of apparently different images (sample IDs: 1 to 100). The correlation value differs depending on the sample, so that it is difficult to determine matching success or failure with a single score acceptance (threshold value) 202 (or 203). When the score acceptance (a first threshold value) 202 is used, the correct matching position of the samples in section 205 will be erroneously determined as being a incorrect matching position.

On the other hand, when the acceptance 203 (a second threshold value) is used, for example, the samples at a incorrect matching position (the hatched region to the right of 205) will be erroneously determined as being at a correct matching position.

Thus, when the score separation between the correct matching position and the incorrect position is poor (so that separation by a unified score is impossible), it becomes difficult to determine matching success or failure, possibly making it impossible to obtain matching performance required by the inspection device.

Further, in the feature point-based template matching, a feature quantity-using method such as scale-invariant feature transform (SIFT) (see Non Patent Literature 2) has been proposed. However, by this technique too, if the apparent discrepancy between the template and the searched image is large, the similarity of feature vectors (feature descriptors) of the template and the searched image becomes poor, preventing successful corresponding point matching and destabilizing matching.

An object of the present invention is to output an accurate matching position in template matching even when the apparent image discrepancy between the template and the searched image is large.

Solution to the Problem

In order to solve the problem, according to the present invention, not only feature quantities (hereafter referred to as "individual feature quantities") are separately extracted from a template or each searched image and compared, but also mutual information (hereafter referred to as "mutual feature quantity") determined from both the template and the searched image is used as information for matching success or failure determination. The outline of a representative example of the present invention for realizing the above is as follows.

An inspection device that performs template matching according to the present invention includes a feature region extraction process unit that extracts from a template a feature quantity determined by a coordinate in an image; a feature quantity extraction process unit that extracts from a searched image a feature quantity determined by a coordinate in the image; a mutual feature quantity calculation process unit that calculates, from the feature quantity extracted from the template, the feature quantity extracted from the searched image, and relative positions of the template and the searched image, a mutual feature quantity of both the template and the searched image; and a template matching process unit that performs matching between the template and the searched image, using a plurality of the mutual feature quantities.

The inspection device may be characterized in that a plurality of types of the mutual feature quantities are used; a plurality of types of the individual feature quantities are also used; in a feature quantity space spanned by the feature quantities, a distance between the coordinate of a matching object and an discrimination surface determining matching success or failure is used as a matching score; and the score is zero (or a score central value is determined) when the distance from the boundary surface is zero), wherein a positive score indicates correct matching whereas a negative score indicates incorrect matching (or, a value greater than the score central value indicates correct matching whereas a value lower than the score central value indicates incorrect). Thus, it becomes possible that the score acceptance has a fixed value of zero (or score central value) at all times.

The present specification incorporates the contents described in the specification and/or drawings of JP Patent Application No. 2012-167363, which is the basis of priority claim by the present application.

Advantageous Effects of Invention

According to the present invention, an accurate matching position can be output in template matching even when there is a large apparent image discrepancy between the template and the searched image.

BRIEF DESCRIPTION OF DRAWINGS

FIGS. 6A and 6B illustrate the principle of a process of calculating the matching score according to the present embodiment.

FIGS. 7A and 7B illustrate a means for designating a matching success/failure decision boundary surface according to the present embodiment (a), and the outline of the process (b).

FIGS. 9A and 9B illustrate a second class feature quantity and a third class feature quantity.

FIGS. 11A and 11B illustrate the calculation of the third class feature quantity.

FIGS. 14A and 14B illustrate a means for providing learning data in the present embodiment.

FIGS. 16A-16C illustrate an example of manually designating the matching success/failure decision boundary surface according to the present embodiment.

FIGS. 17A-17C illustrate a means for confirming matching result stability according to the present embodiment.

DESCRIPTION OF EMBODIMENTS

Figure 1:
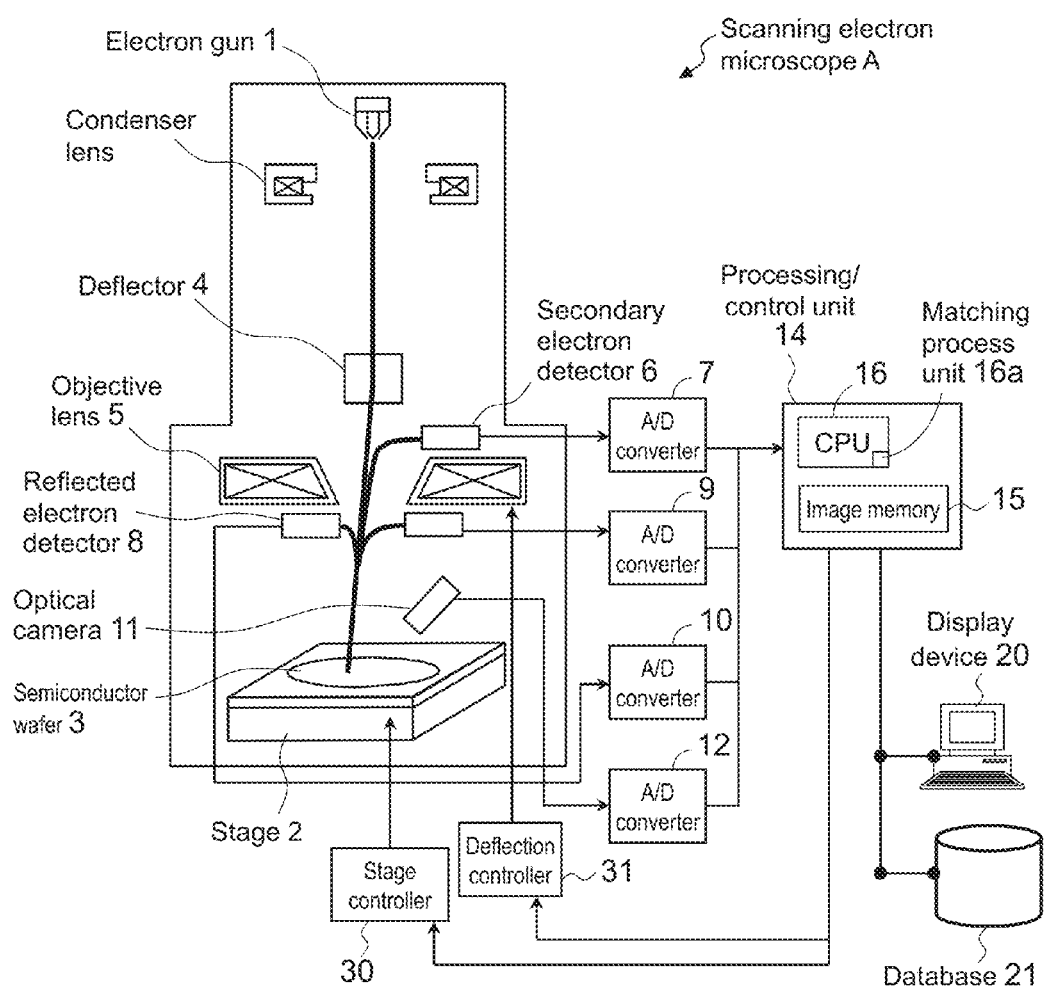
FIG. 1 illustrates an example of an inspection device (SEM) for performing template matching according to an embodiment of the present invention.

In the following, embodiments of the present invention will be described with reference to the drawings. In the drawings, identical reference numerals designate identical members unless otherwise specifically noted.

FIG. 1 illustrates a configuration example of a device for performing template matching using a mask process in a scanning electron microscope (SEM) mainly used for measuring the pattern size of a semiconductor device formed on a semiconductor wafer, as an example of application of an inspection device according to an embodiment of the present invention. In the scanning electron microscope (SEM) A, an electron gun 1 generates an electron beam. The electron beam is focused by controlling a deflector 4 and objective lens 5 so that a sample disposed on a stage 2, such as a semiconductor wafer 3, can be irradiated at a desired position. From the semiconductor wafer 3 irradiated with the electron beam, secondary electrons are emitted, which are detected by a secondary electrons detector 6. The detected secondary electrons are converted into a digital signal by an A/D convertor 7, stored in an image memory 15 in a processing/control unit 14, and subjected to an image process in a CPU 16 in accordance with a purpose. The template matching process according to the present embodiment is executed in the processing/control unit 14, or more specifically, in a matching process unit 16a. Settings for a process which will be described with reference to FIG. 13, and display of a processing result are made on a display device 20. For alignment using an optical camera with lower magnification than the electron microscope, an optical camera 11 is used. A signal obtained by imaging the semiconductor wafer 3 with the camera 11 is also converted into a digital signal in an A/D convertor 12 (the A/D convertor 12 may not be used when the signal from the optical camera is a digital signal), stored in the image memory 15 in the processing/control unit 14, and subjected to an image process in the CPU 16 in accordance with a purpose.

When a reflected electron detector 8 is provided, reflected electrons emitted from the semiconductor wafer 3 are detected by the reflected electron detector 8, and the detected reflected electrons are converted into a digital signal by an A/D convertor 9 or 10, stored in the image memory 15 in the processing/control unit 14, and subjected to an image process in the CPU 16 in accordance with a purpose. In the present embodiment, the scanning electron microscope is described as an example of the inspection device. However, the device to which the present invention is applied is not limited to the above. For example, the present invention may be applied to an inspection device that acquires an image and performs a template matching process.

Figure 2:
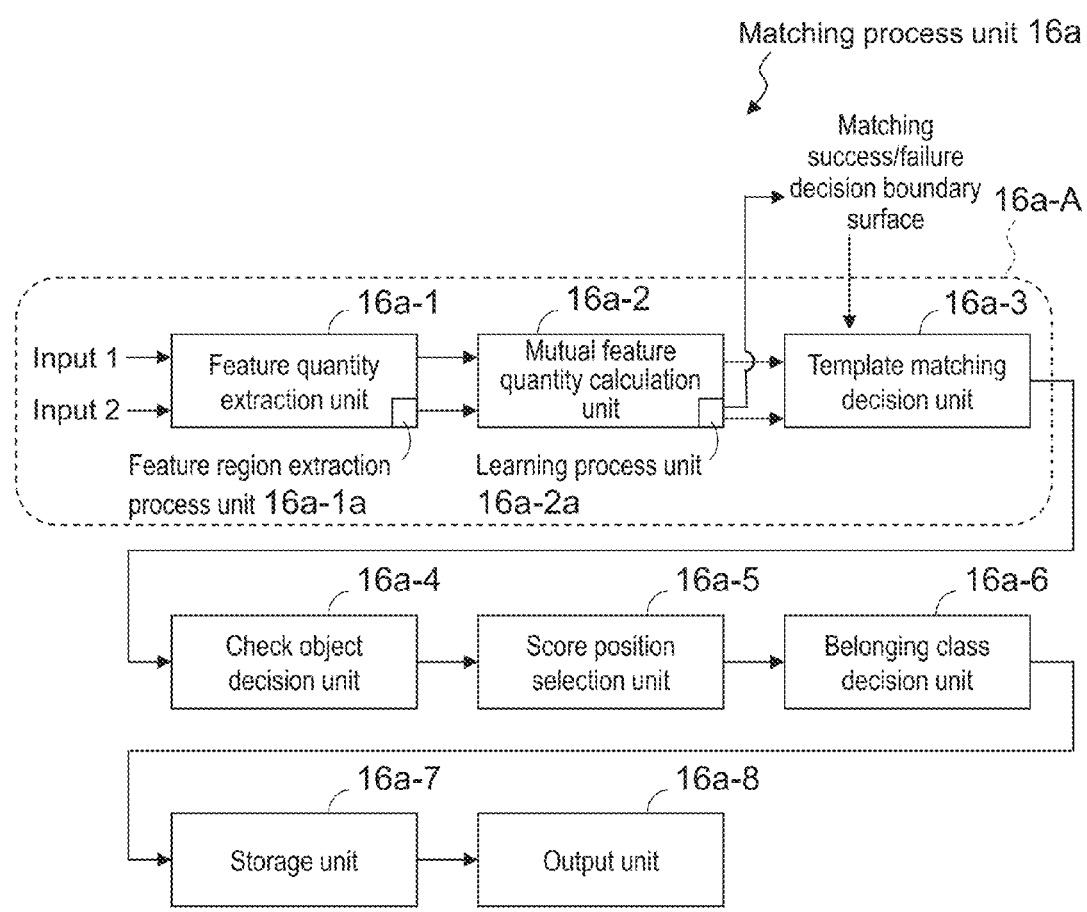
FIG. 2 is a functional block diagram of a configuration example of a template matching process unit according to an embodiment of the present invention.
Figure 3:
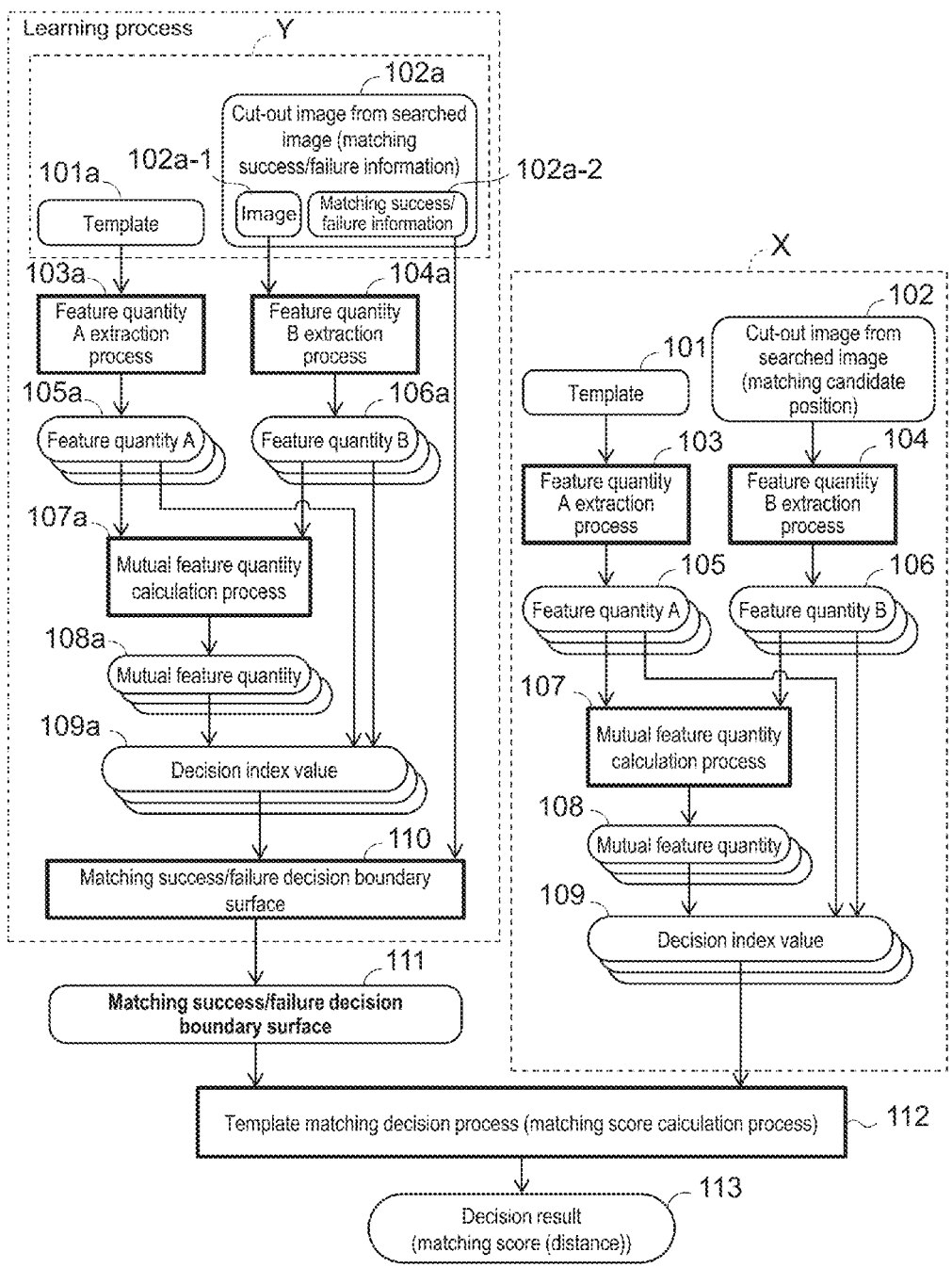
FIG. 3 is a functional block diagram of a configuration example of a template matching device according to an embodiment of the present invention, showing an example of a device having a learning process function.
Figure 4:
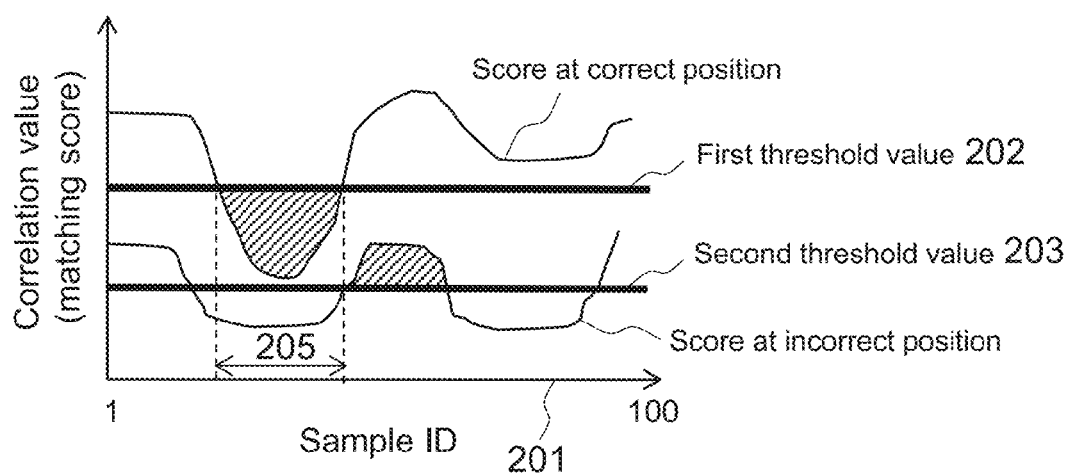
FIG. 4 illustrates an example of correlation values (matching scores) at a correct matching position and a incorrect matching position with respect to a plurality of images (sample IDs: 1 to 100) with different appearances.
Figure 5:
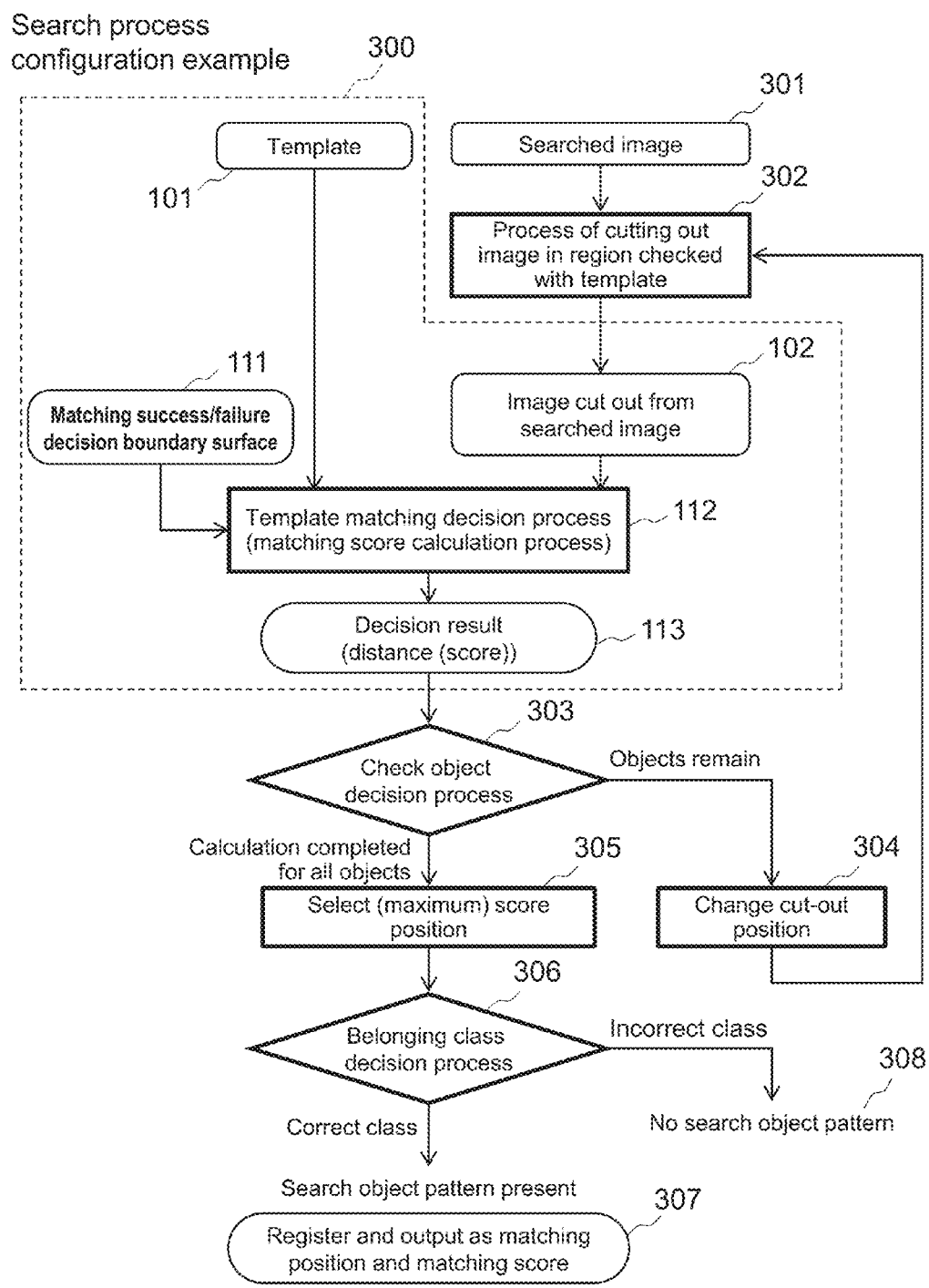
FIG. 5 is a block diagram of a configuration example of a pattern matching process according to the present embodiment.

FIG. 2 is a functional block diagram of a configuration example of the matching process unit in the inspection device according to the present embodiment, specifically a functional block diagram of the process unit for executing a process corresponding to FIG. 5. FIG. 3 is a functional block diagram of an overall configuration example including the flow of the template matching process in the inspection device according to the present embodiment, the figure also illustrating a configuration for a learning process. The learning process and the matching process may be separate processes, involve partly common hardware or software configurations, or a combination of the above.

As illustrated in FIG. 2, the matching process unit 16a shown in FIG. 1 includes: a feature quantity extraction unit 16a-1 that extracts two input feature quantities, for example; a mutual feature quantity calculation unit 16a-2 that calculates a mutual feature quantity indicating a feature quantity relationship on the basis of a plurality of feature quantities including first and second feature quantities; a template matching decision unit 16a-3 that performs template matching determination on the basis of the mutual feature quantity and a matching success/failure decision boundary surface, and that determines a distance (score) between the mutual feature quantity and the matching success/failure decision boundary surface in a feature quantity space; a check object decision unit 16a-4 that determines whether there are remaining check objects; a score position selection unit 16a-5 that selects a position on a wafer where the distance (score) is at a maximum, for example; a belonging class decision unit 16a-6 that makes a correct class/incorrect class determination; a storage unit 16a-7 that stores a matched position (x,y) on the wafer and the like in association with the matching score and the like; and an output unit 16a-8 that outputs a display and the like based on the stored values. The matching process unit 16a further includes, with regard to a learning process which will be described later, a feature region extraction process unit 16a-1a that extracts a feature quantity from a template image acquired for learning, and a learning process unit 16a-2a which will be described later. The matching process unit 16a may be provided with all of the elements (function units) shown in FIG. 2, or with only some of the units.

FIG. 3 is a flowchart illustrating the flow of a process by the matching process unit 16a in the inspection device according to the present embodiment.

As illustrated in FIG. 3, the process according to the present embodiment includes a decision index value calculation process X based on the mutual feature, a correct/incorrect matching decision boundary surface (discrimination boundary surface) designation process Y based on the learning process, and a process of deriving a result of determination by a template matching process based on the process X and the process Y.

The decision index value calculation process X based on the mutual feature is a process of determining a decision index value 109 used for template matching from a pre-registered template 101 and an image 102 cut out from a searched image acquired by the inspection device (a cut-out image at a matching candidate position).

The details of the process of determining whether there is a search object pattern in the searched image, and of the means for determining the matching position will be described later with reference to FIG. 6. In the present embodiment, one of the purposes is to perform successful pattern matching even when, for example, there is a large apparent image discrepancy between the template 101 and the correct matching position of the searched image 102. More specifically, as will be described in the latter half of the description of FIG. 3, a mutual feature quantity 108 determined by using both images of the template 101 and the searched image 102 is used to determine a decision index value 109 for performing feature quantity-based matching. This allows for the implementation of matching by a feature quantity that is not readily subject to the adverse influence of the apparent difference between the template 101 and the searched image 102 (or, matching using a feature quantity so as to avoid the adverse influence), which has been difficult to handle by the feature quantity-based matching using an individual feature quantity determined from only the template 101 or only the searched image 102. Thus, robustness of the template matching can be increased.

The mutual feature quantity 108 is determined by a mutual feature quantity calculation process 107 in the mutual feature quantity calculation unit 16a-2 using a feature quantity A105 extracted from the template 101 by a feature quantity A extraction process 103 by the feature quantity extraction unit 16a-1 and a feature quantity B106 extracted from the cut-out image (matching candidate position) 102 from the searched image by a feature quantity B extraction process 104 by the feature quantity extraction unit 16a-1. The method of calculating the mutual feature quantity will be described later. In a simple calculation method, for example, the template 101 and the cut-out image 102 from the searched image may be used as is as the feature quantity A105 and the feature quantity B106, and a normalized correlation value of the images can be used as one of mutual feature quantities.

For example, an average value of the product of deviations from an average of two sets of corresponding data x and y, namely, covariance $\rho_{XY}$, may be determined as the mutual feature quantity.

$$\rho_{XY} = Cov(x,y)/V(x)^{1/2} \cdot (V(y))^{1/2}$$

The determined mutual feature quantity 108 is used as part or all of the decision index value 109 used in the template matching decision unit 16a-3 (matching score calculation unit). The mutual feature quantity 108 is not limited to a single quantity; a plurality of different types of feature quantities may be calculated and used. The feature quantity B106 extracted from the cut-out image 102 from the searched image may be used as is as a part of the decision index value 109 as an individual feature quantity. This feature quantity is also not limited to a single quantity, and a plurality of different types of feature quantities may be calculated and used as individual feature quantities. The matching score determination process unit may include a central value setting process unit for setting zero distance as the central score value, so that incorrect matching is recognized below the matching score central value or correct matching is recognized above the score central value.

Meanwhile, in the learning process unit 16a-2a, as a template 101a and a cut-out image (correct/incorrect matching information) 102a from the searched image, an image 102a-1 and correct/incorrect matching information 102a-2 may be used. The following process Y for determining a decision index value 109a is similar to the process X and may be executed by the same algorithm or processed by the same hardware. A separate configuration may also be used.

In the process Y, a correct/incorrect matching decision boundary surface designation process 110 is performed on the basis of the decision index value 109a.

In the correct/incorrect matching decision boundary surface designation process 110, while the details will be described later, a boundary surface that determines correct or incorrect matching in a decision index value space is designated. Because a plurality of decision index values are used and the decision index values include the decision index value 109a determined on the basis of the mutual relationship between the template and the searched image, the technique according to the present embodiment increases the probability of determining the matching success/failure decision boundary surface capable of distinguishing matching success or failure even in a case where, for example, matching success or failure cannot be distinguished by only using a correlation value by an image-based matching technique. Using the correct/incorrect matching decision boundary surface 111 designated in the correct/incorrect matching decision boundary surface designation process 110 in the learning process unit 16a-2a, and the decision index value 109 determined by the mutual feature quantity calculation process, a template matching determination process 112 in the template matching decision unit 16a-3 calculates the distance of the decision index value 109 from the matching decision boundary surface in the decision index value space as a matching determination index, the distance providing a determination result (such as a matching score) 113. An example of the distance calculation method will be described later.

As described above, the matching determination index, such as the matching score of the object of matching score calculation (the cut-out image 102 from the searched image) can be calculated. Thus, in the feature quantity-based template matching using the mutual relationship between the template 101 and the searched image 102 also as a feature quantity, it becomes possible to use the learning result of calculation of the discrimination boundary surface determining matching success or failure using a plurality of the mutual feature quantities, enabling a matching process that is not readily subject to the influence of variation with respect to the apparent variation in the searched image.

FIG. 5 is a flowchart illustrating the flow of a search process utilizing the template matching process described with reference to FIG. 3. A portion 300 enclosed by a broken line corresponds to the process described with reference to FIG. 3, in which the template matching determination process 112 calculates the matching determination result (matching score) 113 using the template 101, the image 102 cut out from the searched image, and the correct/incorrect matching decision boundary surface 111 for the learning process.

From the searched image 301, the image 102 is cut out by the process 302 of cutting out the image of a region to be checked with the template, checked with the template 101, and a determination result 113 is output through the template matching determination process 112. In the check object determination process 303, it is determined whether the determination result 113 has been obtained at all of check object positions in the searched image.

If there are remaining check objects, a cut-out position is determined by a cut-out position modify process 304, and an image is cut out by the process 302 of cutting out the image to be checked with the template. If the determination has been completed for all of the check objects in the check object determination process 303, a certain score, such as a maximum score, position selection process 305 is executed to determine a position at which the matching score is at a maximum. Using the matching score at the check position at which the matching score is at a maximum, a belonging class determination process 306 determines whether the check position of the maximum matching score is a position that can be regarded as a correct match or a position regarded as a incorrect match.

In this process, of which the details will be described later, when the decision index value 109 at the check position of the maximum matching score in the decision index value space belongs to the incorrect matching side (incorrect class) (i.e., when below the score acceptance) with reference to the correct/incorrect matching decision boundary surface, it is determined that there was no search object pattern in the field of view of the searched image. In this case, a process of searching for an alignment pattern around the image position, or interrupting the measurement and informing the user of alignment failure via an alarm, for example, may be performed (incorrect class).

On the other hand, if the decision index value 109 at the check position of the maximum matching score belongs to the correct matching side (correct class) (i.e., more than the score acceptance) with reference to the correct/incorrect matching decision boundary surface, that check position is output as a matching position 307. A matching score may also be output together with the correct/incorrect matching.

Thus, as described above, template matching can be performed using the template matching result, such as a matching score, that has been calculated using the mutual feature quantity described with reference to FIG. 3.

FIG. 6 illustrates the principle of the matching score calculation process 112 described with reference to FIG. 3.

In the present embodiment, FIG. 6(a) illustrates an example in which the two decision index values of the decision index value A and the decision index value B are used. For the matching score, the distance between the coordinates of an object for which a score is calculated and the correct/incorrect matching decision boundary surface 111 in a decision index value space (which is indicated two-dimensionally in the present example) spanned by the decision index values is used (the coordinates in the decision index value space are determined from each decision index value 109). The correct/incorrect matching decision boundary surface 111 is given as a result of the correct/incorrect matching decision boundary surface designation process 110, as described with reference to FIG. 3.

For example, when the object of score calculation is at the triangle 405 in the figure, the distance to the correct/incorrect matching decision boundary surface 111 is a broken line portion 410. As the distance, Euclid distance is used, for example. However, the distance used is not limited to Euclid distance, and any means may be used as long as it is capable of calculating the distance from the correct/incorrect matching decision boundary surface 111.

FIG. 6(b) illustrates the relationship between the distance 410 from the correct/incorrect matching decision boundary surface 111 and a matching score 411. The matching score 411 may be determined by, for example, making the matching score 411 zero when the distance from the correct/incorrect matching decision boundary surface 111 is zero, a positive value when in the correct position class, or a negative value when in the incorrect position class. The relationship between the distance and the score may be linear, as indicated by a line 412 in FIG. 6(b).

While a linear example is described herein, the relationship is not limited to the linear one, and the distance and the score may be related to each other non-linearly. In the inspection device as the object of the present embodiment, correct or incorrect matching may be determined by the score acceptance, as described above. The score acceptance is often required to be determined by the user or device designer, and the matching performance may vary depending on its setting. As described above, when the zero distance corresponds to the score of the fixed value of zero, the setting of the acceptance is not required. In the conventional matching system, when, for example, a correlation value is used in the case of matching using normalized correlation, it is only the correlation value that is equivalent to a determination index, and the correlation value itself becomes the score. In this case, if correct and incorrect matching cannot be distinguished when there is only one value used, as in FIG. 6(a), an appropriate acceptance score cannot be set. According to the present embodiment, such case can also be avoided.

The acceptance score for distinguishing correct from incorrect may not be zero, and an offset value may be provided. According to the present embodiment, an example is described in which the correct/incorrect matching determination is performed two-dimensionally using the two decision index values of the decision index value A and the decision index value B. However, the decision index values are not limited to the two values, and more than two decision index values may be used for the correct/incorrect determination.

FIG. 7 illustrates a designation process 110 for the correct/incorrect matching decision boundary surface 111 described with reference to FIG. 3. The matching success/failure decision boundary surface 111 is set for the purpose of distinguishing the case of correct matching (indicated by circles in FIG. 7(a)) and the case of incorrect matching (indicated by crosses in FIG. 7(a)) in the decision index value space. In this way, in the belonging class determination process 306 described with reference to FIG. 6, it can be determined on which side the matching result is with reference to the matching success/failure decision boundary surface 111, showing whether the matching result is a correct matching position or a incorrect matching position. The matching success/failure decision boundary surface 111 may be determined by a technique used in a support vector machine (SVM).

As will be described below in detail, SVM is an identification technique that uses supervised learning. The matching success/failure decision boundary surface 111 corresponds to a separating hyperplane (which may also be referred to as an discrimination surface) according to SVM. In FIG. 7(a), the matching success/failure decision boundary surface 111 provides the separating hyperplane, with a broken line portion 501 inside the matching success/failure decision boundary surface 111 and a broken line portion 502 outside the matching success/failure decision boundary surface 111 providing what SVM calls a "margin". Points on the margin are referred to as support vectors (of which there is at least one in each of the case of correct matching and the case of incorrect matching).

According to SVM, of the learning data, with reference to those (which are support vectors) that are at positions closest to the other cases, the separating hyperplane is set at a position maximizing the Euclid distance. Namely, the margin from the farthest point of one case to the other case is maximized (margin maximization).

By using the matching success/failure decision boundary surface 111 according to the present embodiment as the separating hyperplane according to SVM, it becomes possible to separate the correct matching case and the incorrect matching case in the feature quantity space even when there are a plurality of decision index values. Namely, matching success or failure determination can be made with reference to the matching success/failure decision boundary surface 111 determined by the present technique.

FIG. 7(b) illustrates the configuration of a process for determining the matching success/failure decision boundary surface 111. First, the plurality of decision index values 109a described with reference to FIG. 5 and a matching success or failure 102-2 are combined to provide one case, and data (learning data) 102a including a plurality of the cases are prepared. The learning data 102a include the correct matching case and the incorrect matching case. Then, based on the learning data, the SVM separating hyperplane is determined using SVM as described above (111), the determined separating hyperplane providing the matching success/failure decision boundary surface 111.

By the above process, the matching success/failure decision boundary surface 111 can be determined from a plurality of decision index values using SVM. The determination of the discrimination surface (separating hyperplane) is not limited to SVM, and any technique may be used as long as the matching success/failure decision boundary surface separating the correct matching case from the incorrect matching case can be determined.

Figure 8:
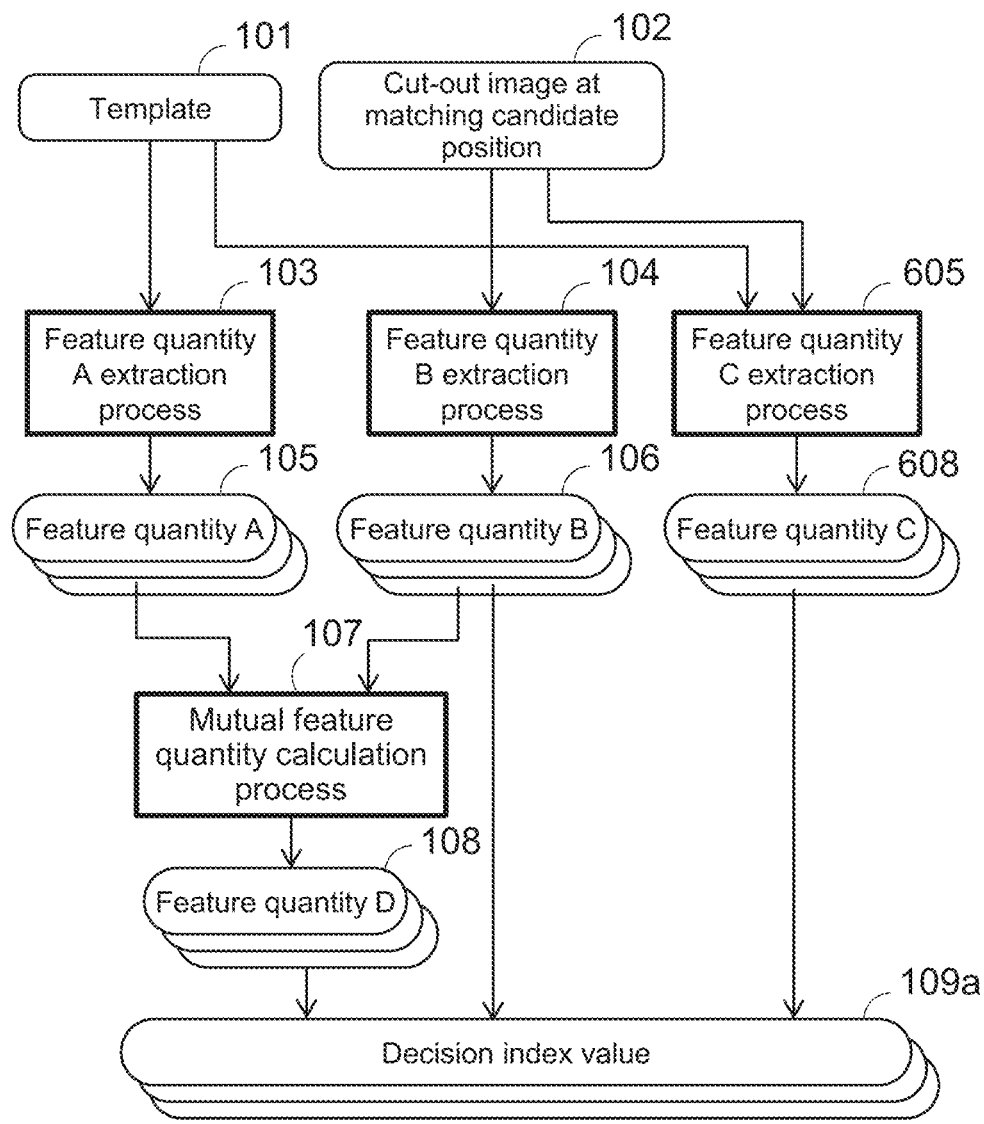
FIG. 8 illustrates the flow of a process of calculating a decision index value according to the present embodiment.

FIG. 8 illustrates the decision index value calculation means described with reference to FIG. 3 and FIG. 5. As described with reference to FIG. 3, the decision index value 109a is calculated from the template 101 and the cut-out image 102 at the matching candidate position.

In the following, first a mutual feature quantity calculation method will be described. A feature quantity (in the present example, the feature quantity A105) extracted from the template 101 by the feature quantity extraction unit A103 and a feature quantity (in the present example, the feature quantity B106) extracted from the cut-out image 102 at the matching candidate position by the feature quantity extraction unit B104 are used to determine a feature quantity D108 in the mutual feature quantity calculation process 107. The method of calculating the mutual feature quantity will be described with reference to FIG. 9. For the individual feature quantities described with reference to FIG. 3, a feature quantity C608 is calculated by a feature quantity extraction process C605 using the cut-out image 102 at the matching candidate position or the template 101. The method of calculating the individual feature quantities will be described with reference to FIG. 9. The determined feature quantity D108 or the feature quantity C608 provides the decision index value 109a. For each of the feature quantity A105, the feature quantity B106, the feature quantity C608, and the feature quantity D108, a plurality of types may be used, in which case a plurality of types of the decision index value 109a would also be used. In the present configuration, a plurality of types of mutual feature quantity and individual feature quantities are determined from the template 101 and the cut-out image 102 at the matching candidate position, and the feature quantities can provide the decision index value 109a.

FIG. 9 illustrates the feature quantity described with reference to FIG. 8. The feature quantity is classified according to its property into what are herein called a first class feature quantity, a second class feature quantity, and a third class feature quantity. The first class feature quantity is a feature that is determined by an object image or a part of the object image in an image of which a feature quantity is calculated, regardless of the position (coordinates) in the image. For example, an average value of the pixel values of the image as a whole, a pixel value variance value and the like provide the first class feature quantities. The present feature quantity is equivalent to the individual feature quantity. The second class feature quantity is a feature quantity determined by the position (coordinates) in the image. For example, as illustrated in FIG. 9(a), at the coordinates (i,j) 1402 (where the origin of the image coordinate system is at the upper-left of the image) on the image, the feature quantity is a calculated feature quantity $V_{i,j}$. Herein, the feature quantity $V_{i,j}$ may be expressed as a multidimensional vector. As illustrated in FIG. 9(a), the feature quantity vector $V_{i,j}$ has vector elements f1 to fn (n is the number of vector elements). For example, a SIFT feature quantity (Non Patent Literature 2) expresses a feature by a vector determined for each of certain coordinates on the image (for each feature point). In the SIFT feature quantity, a region around the feature point is divided into a plurality of small regions (16 regions), and a histogram is generated that has the gradient direction of the pixel values in each small region (8 directions) as a bin. A vector having each bin of each histogram as one vector element (the number of elements is 128 (16×8)) is used as the feature quantity. The present feature quantity is also equivalent to the individual feature quantity.

The third class feature quantity is a feature quantity determined by the second class feature quantity calculated from the template image and the same second class feature quantity calculated from the searched image, and the relative position of the images (such as a check position for the images). A mutual feature quantity is a third class feature quantity. The details of the method for determining the third class feature using the second class feature (a mutual feature quantity calculation method) will be described with reference to FIG. 11 and FIG. 13. For example, as illustrated in FIG. 9(b), the third feature quantity is a feature quantity determined by a relative position 1416 between the template image and a region (broken line portion) cut out from the searched image.

Figure 10:
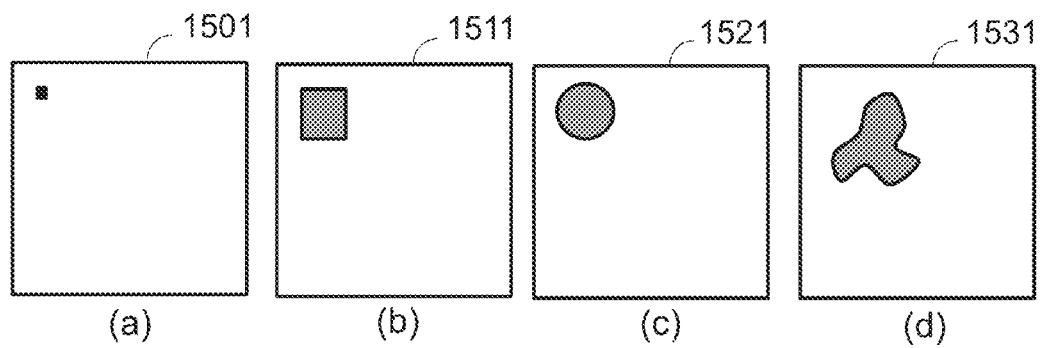
FIGS. 10A-10D illustrate a second class feature quantity calculation region.

FIG. 10 illustrates a feature quantity calculation region for calculating the feature quantity determined by the position in an image with regard to the second class feature quantity described with reference to FIG. 9. FIG. 10(a) illustrates an example of determining the feature quantity from certain coordinates in the image. Pixel values, pixel value gradient information and the like at the coordinates provide the feature quantity. Thus, the feature quantity is determined by the coordinates in the image. FIG. 10(b) illustrates an example of determining the feature quantity from a certain rectangular region in the image. The feature quantity is provided by a pixel value average, pixel value variance, the value of each bin of a pixel value histogram, the value of each bin of a pixel value gradient direction histogram calculated by dividing the rectangular region into small regions, and the like in the rectangular region. In this way, features around the coordinates of interest for calculation of the feature quantity can also be utilized, and more robust matching can be performed using the features. FIG. 10(c) illustrates an example of determining the feature quantity from a circular region in the image. As in the rectangular region of FIG. 10(b), a feature quantity is provided by a pixel value average, pixel value variance, the value of each bin of a pixel value histogram, the value of each bin of a pixel value gradient direction histogram calculated by dividing the circular region into small regions, and the like in the circular region. In this way, features around the coordinates of interest for feature quantity calculation can also be utilized, and more robust matching can be performed by using the features. FIG. 10(d) illustrates an example of determining the feature quantity in a region of a certain desired shape in the image. As in the case of the rectangular region and the circular region of FIGS. 10(b) and 10(c), a feature quantity may be calculated from the region of the desired shape. In this way, features around the coordinates of interest for feature quantity calculation can also be utilized, and more robust matching can be performed by using the features.

FIG. 11 illustrates a method for determining the third class feature quantity from the second class feature quantity, with regard to the third class feature quantity described with reference to FIG. 9. As described above, the third class feature quantity is determined on the basis of the relative position of the second class feature quantity of the template image and the same second class feature quantity of the searched image.

In FIG. 11(a), a region (broken line portion) 1610 of the same size as a template image 1601 is cut out from a searched image 1605 (cut-out position (X,Y) 1607), and a second class feature quantity is calculated from the cut-out region. The same second class feature quantity is also calculated from the template image 1601. A mutual relationship between the second class feature quantity calculated from the searched image 1605 and the second class feature quantity calculated from the template image 1601 is determined to provide the mutual feature quantity. For example, the value of the distance of vectors representing the both second class feature quantities provides the mutual feature quantity. The distance may include Euclid distance, Manhattan distance, or Bhattacharyya distance, and is not particularly limited as long as the relationship between the both feature quantities can be quantized. Thus, the mutual feature quantity is a feature quantity determined by the relative position of the template image and the searched image (in the present example, the image cut-out position (X,Y) 1607 in the searched image corresponds to the relative position).

FIG. 11(b) illustrates a method for determining the relative position of the template image and the searched image, which is a different method from the method of FIG. 11(a). The present method is a method whereby, as a technique for estimating to which position the template image is similar in the searched image, the vote value in the case of a vote based technique is used as the third class feature quantity. In each of the template image and the searched image, the second class feature quantity is calculated (herein the calculation of the second class feature quantity in the searched image has the image region as a whole as the object). In the template image, a point 1631 as a position reference when determining the second class feature quantity will be referred to as a reference point (for example, in FIG. 11(a), when the origin O is at the upper-left of the image coordinate system and the second class feature quantities is determined with reference to the origin, the origin O is the reference point). Of the second class feature quantities of the both images, the feature quantities with the highest similarity are selected and stored as a pair. Based on the distance from the second class feature quantity calculation position (coordinates) in the template image to the reference point, and the vector direction, the coordinates corresponding to the distance determined in the template image and the vector direction (the coordinates estimated to be the position of the template image reference point in the searched image) are determined with respect to the second class feature quantity calculation position (coordinates) on the searched image side paired with the second class feature quantity in the template image. Then, voting is conducted with respect to the determined coordinates as matching position candidate coordinates (one vote for one pair). The voting process is conducted for all of the pairs (or all of the pairs having more than a certain similarity). When a region corresponding to the template image is cut out from the searched image and used as a matching candidate, the number of votes at the reference point (such as at the upper-left coordinates in the cut-out region) 1641 for the cut-out region provides the third class feature quantity. While in the above example the feature point having the highest similarity is selected, several sets having high similarity at each feature point may be used (for example, the upper three sets are used).

From the above, the third class feature quantity can be calculated from the second class feature quantity. By using the third class feature quantity which is a mutual feature quantity, more robust matching can be performed.

Figure 12:
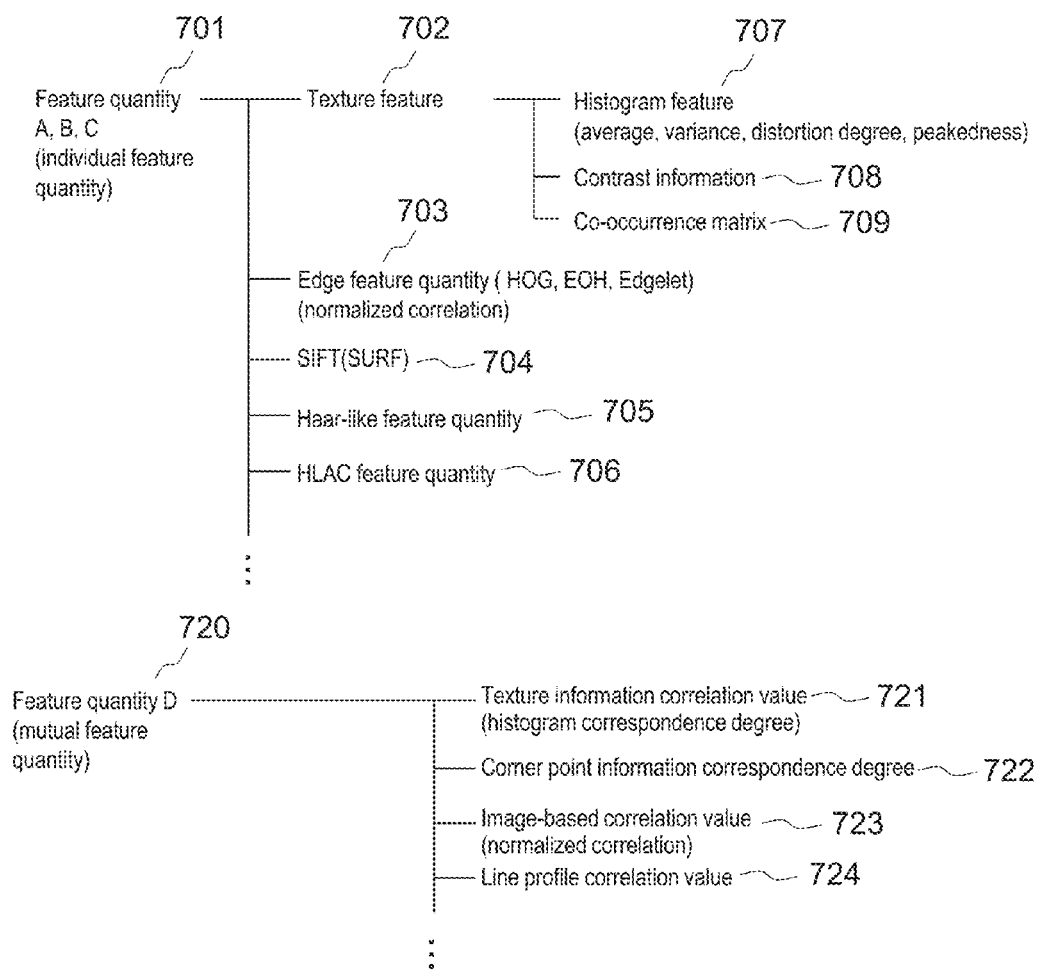
FIG. 12 illustrates an example of the decision index value according to the present embodiment.

FIG. 12 illustrates a concrete example of the feature quantity described with reference to FIG. 8. The feature quantity A105, the feature quantity B106, and the feature quantity C608 (individual feature quantities) described with reference to FIG. 8 of the same type may be used. As illustrated in FIG. 12, as the feature quantity A105, the feature quantity B106, and the feature quantity C608, a feature quantity 702 relating to a texture in the region with reference to certain designated coordinates in the image, or an edge feature quantity 703 representing the information of the structure of a pattern visible in the image may be used, for example. Examples of the feature quantity relating to texture will be described later and may include a histogram feature quantity 707, a contrast feature quantity 708, and a co-occurrence matrix 709. The present feature quantities are feature quantities corresponding to the second class feature quantity described with reference to FIG. 9.

The above is not a limitation, and any technique or feature quantities that enable the extraction of the texture information may be used. The histogram feature 707 includes feature quantities such as an average, variance, distortion degree, or peakedness obtained by analyzing a gradation value histogram in a region with reference to certain designated coordinates in the image in both the template and the searched image. The contrast feature quantity 708 includes the feature quantity of an average gradation value of a designated region in each of the template and the searched image. The designated region includes, for example, a region in which a pattern (such as a line pattern) is present in the image, or a region in which a pattern is not present (underlayer region). Alternatively, a contrast difference between a plurality of designated regions within the field of view of each of the template and the searched image may be determined (contrast feature in the images), and the contrast difference value may be used as a feature quantity. There is also feature point information 704 and the like determined by a technique such as SIFT (Non Patent Literature 2). The edge feature quantity 703 includes feature quantities such as a histogram of oriented gradients (HOG).

On the other hand, the feature quantity D (mutual feature quantity 720) is mutually calculated from the feature quantity A105 and the feature quantity determined from the feature quantity B106. As will be described with reference to FIG. 13, a histogram feature, for example, has a feature quantity of the correspondence degree (such as a value difference) of averages, variance, distortion degrees, or peakedness obtained by analyzing a histogram determined from each of the template and the searched image. Alternatively, a correlation value of the shape of the distribution of the histogram determined from each of the template and the searched image may be used as a feature quantity. In the case of contrast information, a correspondence degree (such as a value difference) of the contrast features determined from each of the template and the searched image may be used as a feature quantity. The correlation value of the template and the searched image themselves may be used as a feature quantity. In this case, the image used may be the input image itself, or an image that has been subjected to preprocessing, such as a noise removing process or an edge enhancing process, may be used. When the mutual feature quantity is determined from corner time point information, the number of corresponding corner points determined in each of the template and the searched image may be used. Alternatively, when the feature point determined by SIFT is used, the voting number in the corresponding point matching described in Non Patent Literature 2 may be used as a feature quantity. The present feature quantity corresponds to the third class feature quantity described with reference to FIG. 9.

Some or all of the above-described plurality of individual feature quantities 701 and the mutual feature quantity may be used for the template matching described with reference to FIG. 3 and FIG. 5.

FIG. 13 illustrates an example of a means for calculating the feature quantities described with reference to FIG. 12. As the feature quantity A105, the feature quantity B106, and the feature quantity C608 described with reference to FIG. 8 and FIG. 12, any of the feature quantities described below may be used.

Figure 13A:
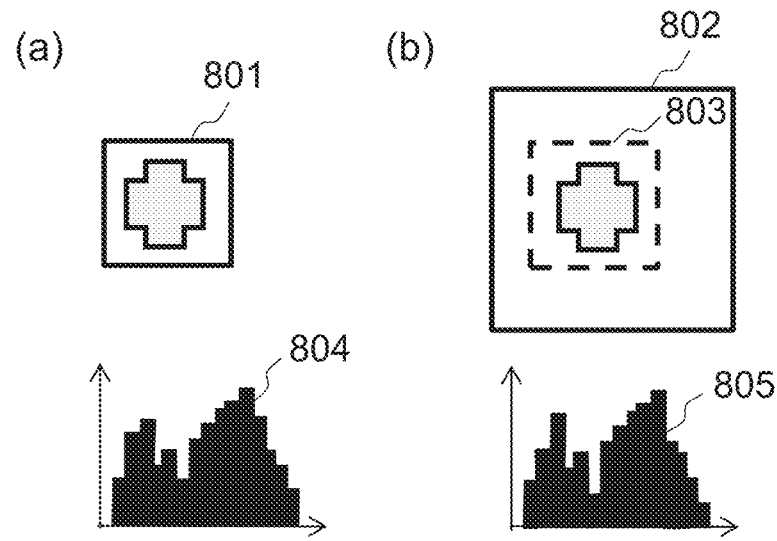
FIG. 13A illustrates an example of the feature quantity according to the present embodiment.

FIG. 13A illustrates a histogram feature. The histogram feature is a means that uses a distribution shape of a gradation value histogram in a designated region, or a value obtained by analyzing the distribution of as a feature. From a template 801 and an image 803 cut out from a searched image 802, histograms 804 and 805 are respectively determined. As feature quantities, the distribution shapes of the histograms may be used as is. For example, a vector having the frequency of each bin (data range divided section) in the histogram as an element provides a feature. Alternatively, some or all of an average, variance, distortion degree, and peakedness calculated by analyzing the distribution shape may be used as feature quantities. As the gradation value histogram, a cumulative histogram may be used.

Figure 13B:
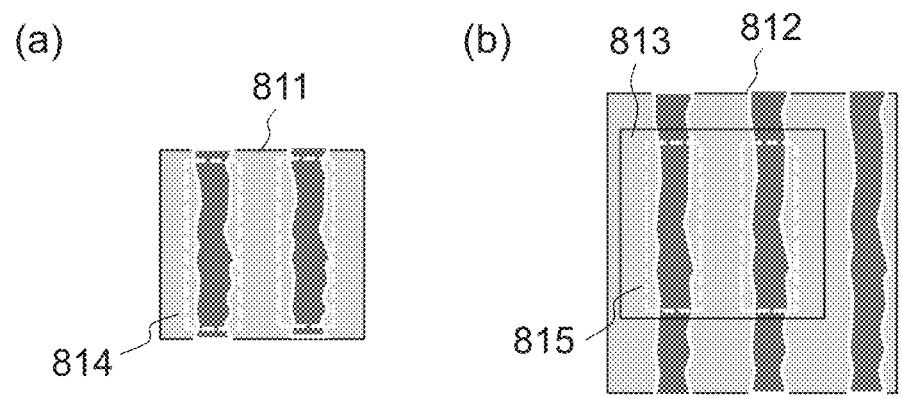
FIG. 13B illustrates an example of the feature quantity according to the present embodiment.

FIG. 13B illustrates a contrast feature. In a template 811 and an image 813 cut out from a searched image 812, an average value of the gradation value in designated regions 814 and 815 is used as the feature quantity. The average value is not a limitation, and any information capable of representing the information of the gradation values in the region may be used, such as a variance value, a maximum value, or a minimum value.

Figure 13C:
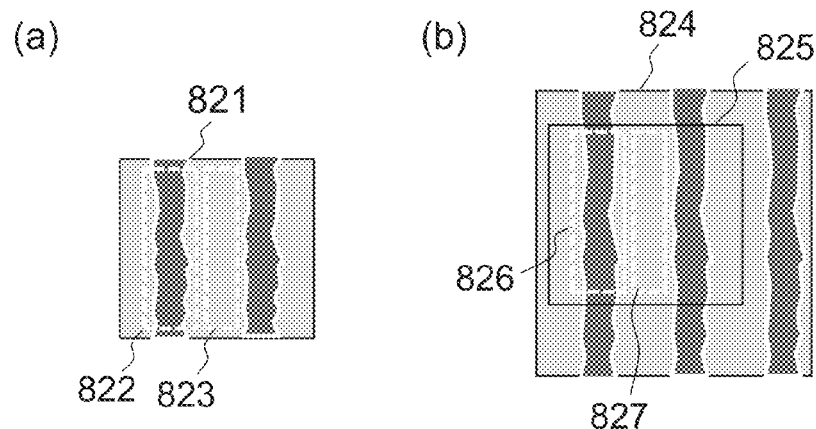
FIG. 13C illustrates an example of the feature quantity according to the present embodiment.

FIG. 13C illustrates a different feature quantity from FIG. 13B with regard to the contrast feature. In a template 821, in each of a plurality of designated regions 822 and 823, the ratio of average values of gradation values (contrast in the image) is determined, and the value of the ratio is used as a feature quantity. Similarly, with respect to an image 825 cut out from a searched image 824, the ratio of average values of gradation values in a plurality of designated regions 826 and 827 (contrast in the image) is used as a feature quantity. While in the present example average values are used, this is not a limitation, and any information capable of representing the information of the gradation values in the region may be used, such as a variance value, a maximum value, or a minimum value.

The feature quantities acquired by the exemplary methods described with reference to FIG. 13A to FIG. 13C are the individual feature quantities that can be used as the feature quantity A105, the feature quantity B106, or the feature quantity C608 described above. Further, as described with reference to FIG. 12, there are also the co-occurrence matrix 709, the edge feature quantity 703, the SIFT feature quantity 704, a Harr-like feature quantity 705, and a HLAC feature quantity 706, for example. These feature quantities, however, are not limitations, and any feature quantity enabling the determination of a value or a vector representing the feature of the template and the image cut out from the searched image may be used.

The mutual feature quantity, i.e. the feature quantity D720 described with reference to FIG. 8 and FIG. 12, can be determined by comparing the individual feature quantities determined from the template image and the image cut out from the searched image.

For example, in the case of the histogram feature quantity determined in FIG. 13A, the mutual feature quantity is provided by a correlation value of the distribution shapes of histograms determined from the template image and an image cut out from the searched image. Alternatively, the mutual feature quantity may be provided by a difference or ratio of average (or variance, distortion degree, or peakedness) values obtained by analyzing the histograms. Also, with regard to the feature quantity of the contrast determined in FIG. 13B and FIG. 13C, the mutual feature quantity may be provided by the difference or ratio of values determined from the template image and the searched image. As the mutual feature quantity, the following may also be used.

Figure 13D:
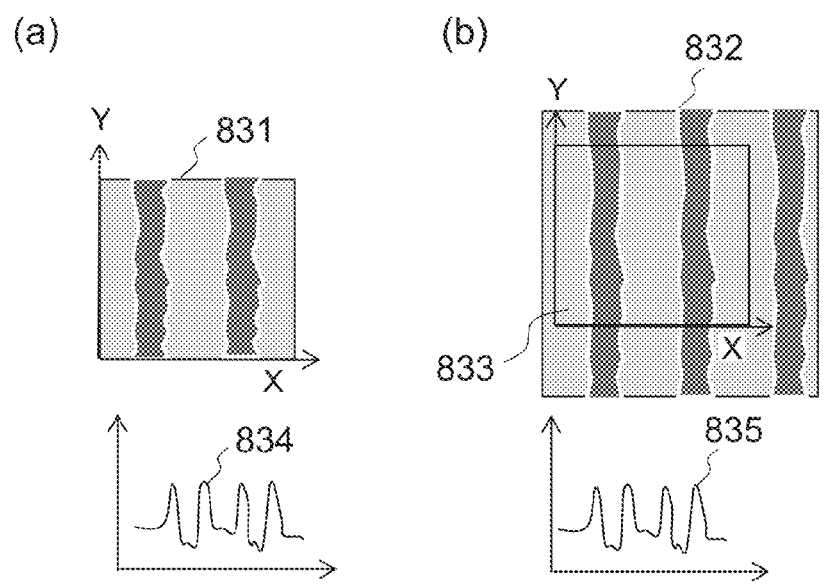
FIG. 13D illustrates an example of the feature quantity according to the present embodiment.

FIG. 13D illustrates a line profile feature. In each of a template 831 and an image 833 cut out from a searched image 832, pixels are averaged (projected) in a certain direction of the image to determine a different dimension waveform, which is referred to as a line profile. FIG. 13D is an example of projection in the Y-direction in both of the images, where the correlation value of line profiles 834 and 835 of the images is determined, providing the mutual feature quantity. The range in which the correlation is determined from line profiles is not limited to the line profiles as a whole, and the correlation value of only a section cut out from a part of the line profile may be used.

Figure 13E:
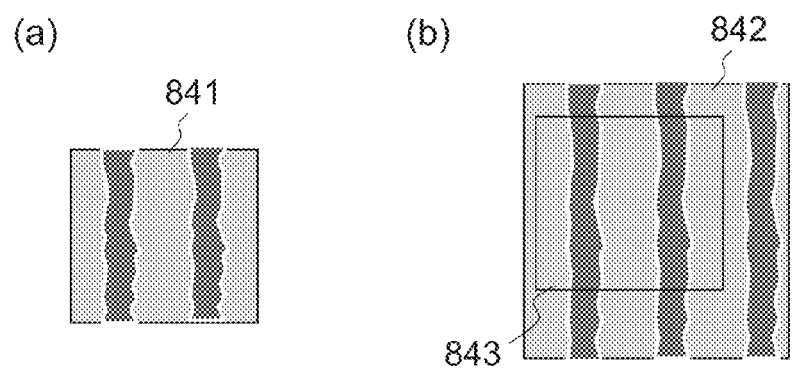
FIG. 13E illustrates an example of the feature quantity according to the present embodiment.

FIG. 13E illustrates an example of using a correlation value of images themselves as a mutual feature quantity. A correlation value between images is calculated from a template 841 and an image 843 cut out from a searched image 842, and the correlation value is used as a feature quantity.

Figure 13F:
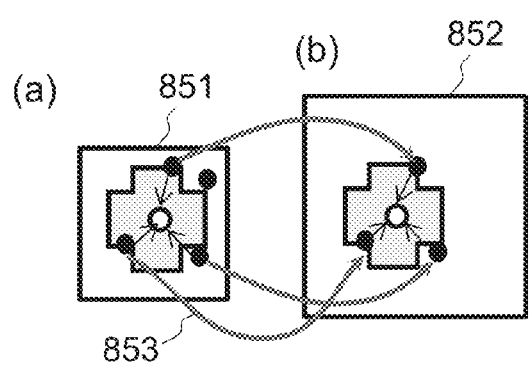
FIG. 13F illustrates an example of the feature quantity according to the present embodiment.

FIG. 13F illustrates an example of using a corresponding point matching result according to SIFT as a mutual feature quantity. When corresponding point matching (for example, corresponding points 853 are connected by an arrow) is performed at feature points (feature descriptors) extracted from a template 851 and a searched image 852, the coordinates, scale and the amount of rotation of the corresponding feature point in the searched image 852 are determined (Non Patent Literature 2). In the template 851, reference point coordinates (such as the position of the white circle in the template 851) is determined, and voting (voting process) is performed at the position of the reference point in the searched image 852 on the basis of the information of the coordinates, scale, and the amount of rotation, as in generalized Hough transform (Non Patent Literature 2). A feature quantity may be provided by the number of votes that the template is projected at (or around) the position of the image cut out from the searched image. Instead of the number of votes, a peripheral region may also be taken into consideration and the density of the votes (the number of votes/area of the peripheral region) may be used. A correlation value between a SIFT feature quantity of the template and a SIFT feature quantity in the searched image at the corresponding points at which the corresponding point matching was performed may provide a feature quantity.

Figure 13G:
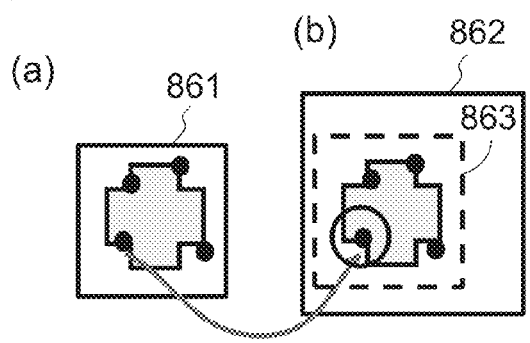
FIG. 13G illustrates an example of the feature quantity according to the present embodiment.

FIG. 13G illustrates an example of using a corner corresponding point matching result as a mutual feature quantity instead of the SIFT of FIG. 13F. When corresponding point matching is performed using corners extracted from each of a template 861 and an image 863 cut out from a searched image 862 as feature points (for example, corresponding points are connected by an arrow), the coordinates, scale, and the amount of rotation of a corresponding feature point in the searched image 862 are determined.

By the above method, a mutual feature quantity can be determined. The method of calculating the mutual feature quantity is not limited to the above method, and any feature quantity (such as a scalar value or a vector) that represents the mutual relationship between the template and the searched image may be used.

The template and the searched image may be subjected to preprocessing to generate noise-reduced or feature-enhanced images, and the above-described feature quantities (the individual feature quantities and the mutual feature quantity) may be determined with respect to the generated images. The preprocessing may include but are not limited to smoothing filtering, edge enhancing filtering, and binarizing process. Any filtering process that can be used as preprocessing may be used. A process combining a plurality of types of preprocessing may be performed with respect to the template or the searched image, and the above-described feature quantities (the individual feature quantities and the mutual feature quantity) may be determined with respect to the image obtained by the process.

By using the above-described mutual feature quantity and a plurality of individual feature quantities as discrimination index values, matching success/failure determination can be successfully performed even in a case where, conventionally, matching success/failure determination fails with only the individual feature quantities. This is an advantage arising from the fact that the matching success/failure discrimination boundary surface can be determined in a discrimination index value space so that, by using the information of the mutual relationship of the template and the searched image also as a discrimination index value, changes in the mutual relationship between the template and the searched image can be absorbed.

FIG. 14 illustrates in detail the learning data used for calculating the matching success/failure decision boundary surface 111 described in FIG. 7. FIG. 14(a) is an example of simple learning data, where a single template 1001, an image 1002 cut out from the searched image at a correct matching position, and an image 1003 cut out from a incorrect matching position are used as learning data. The image cut out from the searched image (correct position and incorrect position) may include a plurality of images if such images can be obtained from a single image. Alternatively, when a plurality of images is used for learning (with a common template), one or a plurality of images may be cut out from each of a plurality of images used for learning. When the number of the cut-out images is increased to increase the number of samples of the template and the searched image with different appearances, it becomes more likely that an increase will be achieved in the generalization capability of the matching success/failure decision boundary surface 111 for discriminating the correct matching position from the incorrect position in the discrimination index value space described with reference to FIG. 7.

FIG. 14(b) illustrates an example of using a plurality of types of templates 1011 used for learning data. By using such a plurality of templates 1004, it becomes possible to determine a matching success/failure decision boundary surface having lower dependency on the pattern or appearance of a specific template, i.e., higher versatility.

Figure 15:
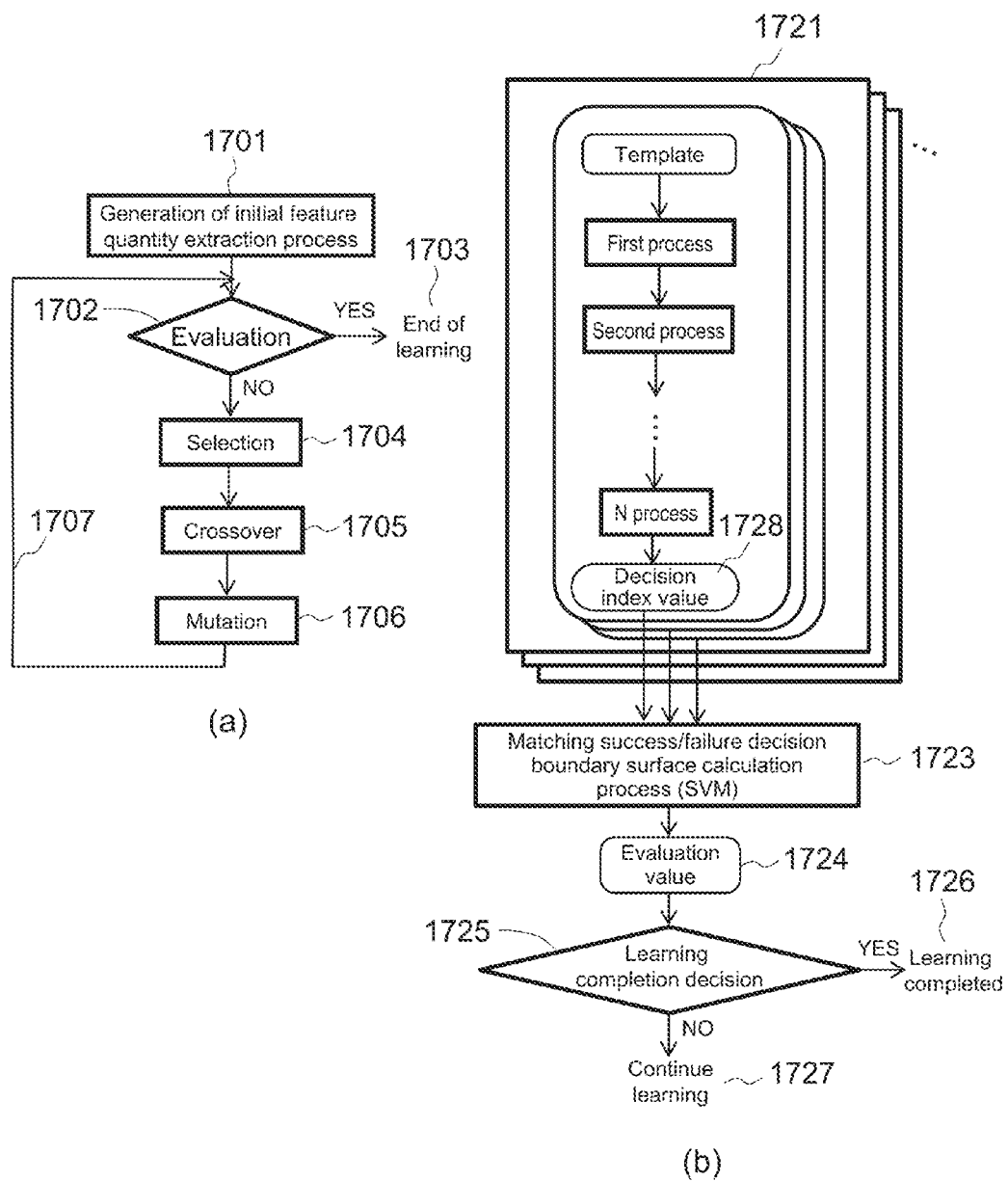
FIGS. 15A and 15B illustrate a method of learning a feature quantity calculation method in addition to the learning of the matching success/failure decision boundary surface.

FIG. 15 illustrates a method whereby, not only the matching success/failure boundary surface is learned in FIG. 3, but also the feature quantity extraction method in the feature quantity extraction unit is determined by learning. In the present example, the feature quantity extraction method is learned according to a genetic algorithm (hereafter referred to as "GA"), or genetic programming (hereafter referred to as "GP"). The feature quantity extraction is constituted by a combination of a plurality of image processes. Each of the image processes may include a plurality of setting parameters. The combination of the image processes, and the set parameters of each process are learned using GA or GP. A combination of image processes (including parameter setting) for calculating a decision index value is a chromosome (solution candidate). FIG. 15(a) illustrates the flow of the process in which GA or GP is used for learning. First, generation 1701 of a plurality of process feature quantity extraction processes (initial chromosome group) is performed. Then, with respect to a genotype, evaluation 1702 for learning completion determination, which will be described later, is performed. If the learning is completed 1703 as a result of the evaluation, the feature quantity extraction method and the matching success/failure decision boundary surface are determined. If it is not determined that the learning is completed, chromosome selection 1704, crossover 1705, and mutation 1706 are performed. With respect to the resultant chromosome group, the evaluation 1702 for learning completion determination is again performed. Until the learning is completed, the present process is repeated (generation update). FIG. 15(*b*) illustrates in detail the evaluation unit of FIG. 15(*a*). As described above, the chromosome 1721 is a combination of processes of calculating a decision index value 1728 (a plurality of decision index values are calculated from one chromosome). A plurality of chromosomes (solution candidates) 1721 is generated (for example, 100 individuals are generated). Based on the decision index value determined for each chromosome (feature quantity extraction process), a matching success/failure decision boundary surface calculation process 1723 is performed. Herein, the matching success/failure decision boundary surface is calculated by SVM described above. As an evaluation value 1724, the distance (score) from the matching boundary surface to a support vector by SVM may be used. Depending on whether the evaluation value satisfies a designated value (for example, whether the distance is greater than the designated value), learning completion determination 1725 is performed. The chromosome at the completion of learning provides the feature quantity extraction method (a combination of image processes and a parameter setting for each image process), and also the matching success/failure decision boundary surface is determined. When learning is not completed, learning is continued and the processes of selection 1704, crossover 1705, and mutation 1706 described with reference to FIG. 15(*a*) are repeated (generational change). While the distance is herein used as the evaluation value, the evaluation value is not limited to the distance and may include any evaluation value as long as the quality of the matching success/failure decision boundary surface can be determined.

As described above, by using GA (or GP) and SVM in combination, it becomes possible to learn not only the matching success/failure decision boundary surface but also the feature quantity extraction process method. The technique used for learning is not limited to GA (or GP) or SVM, and any method capable of the above-described learning may be used.

FIG. 16 illustrates an example of a GUI for realizing manual setting of the matching success/failure decision boundary surface 111. As described above, the matching success/failure decision boundary surface 111 can be determined using a technique such as SVM, for example. In the example of FIG. 16, however, the matching success/failure decision boundary surface 111 is manually designated by the user. FIG. 16(*a*) illustrates an example of user setting on the GUI. In the GUI illustrated in FIG. 16(*a*), the decision index value space is displayed on a display device 20, such as an LCD screen. In the example of FIG. 16(*a*), two decision index values of a decision index value A1103 and a decision index value B1104 are shown in the vertical axis and the horizontal axis of a graph. When three or more decision index values are used, the index values shown in the axes may be switched for display. In the present GUI, a boundary surface draw button 1102 is selected using a mouse and the like to start accepting the user input of a matching decision boundary surface 1101. Then, the user manually draws the decision boundary surface 1101 in the decision index value space of the GUI via mouse input and the like. The matching decision boundary surface drawn by the user can be designated by the user and used as the matching success/failure decision boundary surface 111 described with reference to FIG. 3.

The GUI is not limited to the format illustrated in FIG. 16 and any known technology may be used as long as the matching success/failure decision boundary surface 111 can be manually designated by the user.

FIGS. 16(*b*) and (*c*) illustrates an example of the decision index value space displayed in the GUI. FIG. 16(*b*) illustrates an example in which the correct/incorrect matching decision boundary surface 111 is linearly drawn. FIG. 16(*c*) illustrates an example in which the correct/incorrect matching decision boundary surface 111 is drawn with curves. In the graphs, the plots indicated by circle and cross signs indicate the decision index values in learning data, where each sign corresponds to a decision index value determined from a set of template and an image cut out from the searched image. In the example, the circles indicate correct matching values, while the crosses indicate incorrect matching values. The distribution of the circle and cross signs may be displayed as reference data for the user in designating the matching success/failure decision index values 1103 and 1104 by a manual operation. While in the present example circle and cross signs are used, this is not a limitation, and any sign may be used as long as the correct and incorrect matchings can be distinguished. Thus, even when there is a plurality of matching success/failure decision index values, there can be provided a means for inputting the matching success/failure decision index values 1103 and 1104 manually.

FIG. 17 illustrates an example of GUI for confirming the stability of a matching result in the decision index value space spanned by decision index values. FIG. 17(*a*) illustrates an example of a two-dimensional decision index value space. In the decision index value space spanned by a decision index value A1203 and a decision index value B1204, the GUI displays a position 1202 of a matching result in the decision index value space on the basis of decision index values determined from a matching success/failure decision boundary surface 1201 and the template and the image cut out from the searched image when a check position (matching result) was obtained by matching. By the GUI illustrated in the figure, it becomes possible to graphically confirm how far the matching result is spaced apart from the matching success/failure decision boundary surface 1201. If the matching result is close to the matching success/failure decision boundary surface 1201, it can be confirmed that the correct/incorrect matching may vary if the decision index values are slightly varied, indicating that the matching may be destabilized.

On the other hand, if the matching result is distanced from the matching success/failure decision boundary surface 1201, it can be confirmed that the probability is high that the matching is stable.

FIG. 17(*b*) illustrates an example of GUI for confirming matching result stability, as in FIG. 17(*a*). In this example, a decision index value space spanned by three decision index values can be graphically confirmed in a three-dimensional graph. A matching success/failure decision boundary surface 1205 and the matching result position 1202 can be displayed in the same way as in FIG. 17(*a*).

The matching success/failure decision boundary surface 1205 is such that the data within the boundary surface can be confirmed by transparent display. Viewpoint moving buttons 1206 and 1207, for example, enable confirmation of the position of the learning data, the matching success/failure decision boundary surface, and the matching result in the decision index value space from a desired viewpoint, such as from a front side or a back side.

FIG. 17(c) illustrates a GUI for confirming the matching result stability, as in FIGS. 17(a) and (b). In this example, decision index value spaces spanned by a plurality of decision index values are displayed 1211 such that all or some of the decision index value spaces 1214 spanned by two desired decision index values onto which a matching decision boundary surface is projected are arranged in a corresponding manner. The example of FIG. 17(c) corresponds to a case where there are four decision index values A, B, C, and D (1212, 1213). For example, the decision index value space 1214 obtained from A and B onto which a matching decision boundary surface is projected can be viewed with respect to a desired corresponding relationship. Thus, the GUI enables confirmation of the matching result stability. The location, size, or items of the display members in the GUI are not limited to those illustrated in the figure, and any display method may be employed as long as the positional relationship of the learning data, the matching success/failure decision boundary surface, and the matching result in the decision index value space can be confirmed.

In the foregoing embodiments, the elements and the like are not limited to those illustrated in the attached drawings, and various modifications may be made within the scope in which the effects of the present invention can be obtained. Various other modifications may be made without departing from the scope of the object of the present invention.

Various constituent elements of the present invention may be selectively adopted or not adopted as needed, and an invention provided with the selected elements is also included in the present invention.

INDUSTRIAL APPLICABILITY

The present invention may be utilized for a pattern matching device.

REFERENCE SIGNS LIST

A Scanning electron microscope
14 Process control unit
15 Image memory
16a Matching process unit
16a-1 Feature quantity extraction unit
16a-2 Mutual feature quantity calculation unit
16a-3 Template matching decision unit
16a-4 Check object decision unit
16a-5 Score position selection unit
16a-6 Belonging class decision unit
16a-7 Storage unit
16a-8 Output unit
20 Display device All publications, patents, and patent applications cited herein are incorporated by reference into the present specification in their entirety.

The invention claimed is:

1. A matching process device that performs pattern matching on a searched image, comprising:
a feature region extraction process unit that extracts, from a template image acquired for learning, a region for extraction of a feature quantity determined by a coordinate in the image;
a feature quantity extraction process unit that extracts, from the searched image acquired for learning, a feature quantity determined by a coordinate in the image;
a first mutual feature quantity calculation process unit that calculates a first mutual feature quantity of the template image and the searched image from the feature quantity extracted from the template image, the feature quantity extracted from the searched image, and a relative position of the template image and the searched image;
a discrimination boundary surface calculation unit that calculates a discrimination boundary surface that determines matching success or failure, using a plurality of the first mutual feature quantities calculated from feature quantities with different feature quantity values at the same coordinate in images extracted by a plurality of the feature quantity extraction process units with different feature quantity extracting computations;
a second mutual feature quantity calculation process unit that calculates a second mutual feature quantity from the template image acquired from an inspection object and the searched image;
a template matching process unit that performs matching between the template image of the inspection object and the searched image, using a plurality of the second mutual feature quantities calculated from feature quantities with different feature quantity values at the same coordinate in the images and the discrimination boundary surface;
and a matching success/failure decision boundary surface designation process unit that determines the matching decision boundary surface by using, as an input, the first mutual feature quantity, the feature quantity extracted from the template, the feature quantity extracted from the searched image, and a matching success/failure result between the template acquired in advance and the searched image.

2. The matching process device according to claim 1, wherein the template matching process unit includes a matching score calculation process unit that calculates, as a matching score, a distance from the discrimination boundary surface in a feature quantity space having a plurality of feature quantities.

3. The matching process device according to claim 2, wherein the matching score calculation process unit includes a central value setting process unit that sets the score with a distance of zero as a central value, wherein a distance below the matching score central value indicates incorrect matching and a distance above the score central value indicates correct matching.

4. The matching process device according to claim 1, wherein, in the second mutual feature quantity calculation unit, at least one of a normalized correlation value of the template and the searched image, a correspondence degree of the coordinates of similar feature points between a feature point group extracted from the template and a feature point extracted from the searched image, and a correspondence degree between a gradation value histogram determined from the template and a gradation value histogram determined from the searched image provides a feature quantity.

5. The matching process device according to claim 1, wherein the feature quantity of the matching object and the discrimination boundary surface are displayed on a GUI, and a process is performed, in accordance with the feature quantity of the matching object, for determining the discrimination boundary surface that enables matching process success/failure determination so that a margin can be maximized.

6. An inspection device that performs pattern matching using the matching process device according to claim 1.

7. A matching process method for performing pattern matching on a searched image, the method comprising:
- a feature region extraction step of extracting, from a template image acquired for learning, a region for feature quantity extraction;
- a feature quantity extraction step of extracting a feature quantity from a searched image acquired for learning;
- a first mutual feature quantity calculation step of calculating, from the feature quantity extracted from the template image and the feature quantity extracted from the searched image, a first mutual feature quantity of the template image and the searched image;
- a discrimination boundary surface calculation step of calculating, using a plurality of the first mutual feature quantities, a discrimination boundary surface that determines matching success or failure;
- a second mutual feature quantity calculation step of calculating, from the template image acquired from an inspection object and the searched image, a second mutual feature quantity;
- a template matching step of performing matching between the template image of the inspection object and the searched image by using the second mutual feature quantity and the discrimination boundary surface;
- and a matching success/failure decision boundary surface designation process step of determining the matching decision boundary surface by using, as an input, the first mutual feature quantity, the feature quantity extracted from the template, the feature quantity extracted from the searched image, and a matching success/failure result between the template acquired in advance and the searched image.

8. A matching process device that performs pattern matching on a searched image, comprising:
- a feature region extraction process unit that extracts, from a template image, a region for feature quantity extraction that is determined by a coordinate in the image;
- a feature quantity extraction process unit that extracts, from the searched image, a feature quantity determined by a coordinate in the image;
- a mutual feature quantity calculation process unit that calculates, from the feature quantity extracted from the template image, the feature quantity extracted from the searched image, and a relative position of the template image and the searched image, a mutual feature quantity of the template image and the searched image;
- a template matching process unit that performs matching between the template image of the inspection object and the searched image, using a plurality of the mutual feature quantities calculated from feature quantities with different feature quantity values at the same coordinate in images extracted by a plurality of the feature quantity extraction process units with different feature quantity extracting computations, and a pre-set discrimination boundary surface that determines matching success or failure;
- and a matching success/failure decision boundary surface designation process unit that determines the matching decision boundary surface by using, as an input, the first mutual feature quantity, the feature quantity extracted from the template, the feature quantity extracted from the searched image, and a matching success/failure result between the template acquired in advance and the searched image.

* * * * *